US012208111B2

(12) United States Patent
Sotgia et al.

(10) Patent No.: US 12,208,111 B2
(45) Date of Patent: Jan. 28, 2025

(54) AZITHROMYCIN AND ROXITHROMYCIN DERIVTIVES AS SENOLYTIC DRUGS

(71) Applicant: LUNELLA BIOTECH, INC., Ottawa (CA)

(72) Inventors: Federica Sotgia, Greater Manchester (GB); Michael P. Lisanti, Greater Manchester (GB)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

(21) Appl. No.: 18/442,204

(22) Filed: Feb. 15, 2024

(65) Prior Publication Data

US 2024/0180944 A1    Jun. 6, 2024

Related U.S. Application Data

(62) Division of application No. 17/282,212, filed as application No. PCT/US2019/054231 on Oct. 2, 2019, now Pat. No. 11,957,700.

(60) Provisional application No. 62/788,187, filed on Jan. 4, 2019, provisional application No. 62/750,559, filed on Oct. 25, 2018, provisional application No. 62/740,137, filed on Oct. 2, 2018.

(51) Int. Cl.
| | | |
|---|---|---|
| A61K 31/7048 | (2006.01) | |
| A61K 31/7052 | (2006.01) | |
| A61K 45/06 | (2006.01) | |

(52) U.S. Cl.
CPC ...... *A61K 31/7048* (2013.01); *A61K 31/7052* (2013.01); *A61K 45/06* (2013.01)

(58) Field of Classification Search
None
See application file for complete search history.

(56) References Cited

U.S. PATENT DOCUMENTS

| | | |
|---|---|---|
| 9,180,134 B2 | 11/2015 | Auwerz et al. |
| 2008/0045585 A1 | 2/2008 | Farmer et al. |
| 2014/0187611 A1 | 7/2014 | Auwerx et al. |
| 2015/0190415 A1 | 7/2015 | Lewis et al. |
| 2018/0021323 A1 | 1/2018 | Zhou et al. |

FOREIGN PATENT DOCUMENTS

| | | |
|---|---|---|
| GB | 2472138 | 1/2011 |
| JP | 2006-513157 A | 4/2006 |
| WO | 2004/039821 | 5/2004 |
| WO | 2004-039821 A1 | 5/2004 |
| WO | WO 2008072034 A1 | 6/2008 |
| WO | 2018/129007 | 7/2018 |
| WO | WO 2018193125 A1 | 10/2018 |
| WO | 2018/213764 A1 | 11/2018 |
| WO | 2020/131704 A1 | 6/2020 |

OTHER PUBLICATIONS

International Search Report for PCT/US2019/054231 mailed Mar. 10, 2020, 7 pages.
Written Opinion of the ISA for PCT/US2019/054231 mailed Mar. 10, 2020, 16 pages.
International Preliminary Report on Patentability for PCT/US2019/054231, completion date Jan. 12, 2021, 23 pages.
Ozsvari et al., "Exploiting Mitochondrial Targeting Signals, TPP and bis-TPP, for eradicating cancer stem cells (CSCs)", Aging, Feb. 19, 2018, pp. 229-240.
Kim et al., "Phosphatidylserine-dependent Neuroprotective Signaling Promoted by Docosahexaenoic Acid", Prostaglandins Leuk Essent Fatty Acids, 2010, vol. 82, pp. 1-15.
Tai et al., "Autophagy impairment with lysosomal and mitochondrial dysfunction is an important characteristic of oxidative stress-induced senescence", Autophagy, 2017, vol. 13:1, pp. 99-113.
Tuncbilek et al., "Synthesis of Novel 6-(4-Substituted piperazine-1-yl)-9-(beta-D-ribofuranosyl) purine Derivatives, Which Lead to Senescence-Induced Cell Death in Liver Cancer Cells", J. Med. Chem., 2012, vol. 55, pp. 3058-3065.
Fernandes, P. et al., Nature nurtures the design of new semi-synthetic macrolide antibiotics. *The Journal of Antibiotics*, Nov. 30, 2016, vol. 70, pp. 527-533 Figure 1.
Ozsvari, B. et al., Azithromycin and Roxithromycin define a new family of "senolytic" drugs that target senescent human fibroblasts. *Aging (Albany NY)*, Dec. 11, 2018, vol. 10, No. 11, pp. 3294-3307 the whole document.
Djokic S et al: "Erythromycin Series XII. 1-4,6 Antibacterial in Vitro Evaluation of 10-Dihydr0-10-Deoxo-ll-Azaerythromycin A: Synthesis and Structure-Activity Relatinship of Its Acyl Derivatives", The Journal of Antibiotics, Nature Publishing Group UK, London, vol. 40, No. 7, Jul. 1, 1987 (Jul. 1, 1987), pp. 1006-1015, XP000654487, ISSN: 0021-8820 * p. 1009, right-hand column; compound 6 * * Experimental; p. 1012.

(Continued)

*Primary Examiner* — Layla D Berry
(74) *Attorney, Agent, or Firm* — Nixon & Vanderhye, P.C.

(57) ABSTRACT

This disclosure describes the use of azithromycin, roxithromycin, and telithromycin, including derivatives thereof, as senolytic drugs. BrdU was used to induce senescence in model human fibroblast cell lines. Also disclosed are methods for screening compounds for senolytic activity. The SRB assay was used to measure cell viability through protein content. Azithromycin roxithromycin, and telithromycin, clinically-approved pharmaceuticals, were found to be senolytic drugs. However, the closely-related parent compound, erythromycin, showed no senolytic activity. Azithromycin strongly induced both aerobic glycolysis and autophagy in human fibroblasts, but showed bi-phasic effects including on mitochondrial oxygen consumption rates with inhibitory activity at 50 µM and stimulatory activity at 100 µM. The xCELLigence real-time assay system showed that azithromycin preferentially targets senescent cells, removing approximately 97% (nearly a 25-fold reduction in senescent cells).

8 Claims, 15 Drawing Sheets

(56) References Cited

OTHER PUBLICATIONS

Hubackova Sona et al: "Selective elimination of senescent cells by mitochondrial targeting is regulated by ANT2", Cell Death & Differentiation, Nature Publishing Group, GB, vol. 26, No. 2, May 21, 2018 (May 21, 2018), pp. 276-290, XP036721093, ISSN: 1350-9047, DOI: 10.1038/S41418-018-0118-3 [retrieved on May 21, 2018] * 1st full paragraph; left-hand column—p. 279 * p. 285; figure 5.

Jin, M. et al., Relationship of Absolute Telomere Length With Quality of Life, Exacerbations, and Mortality in COPD. Chest, Jul. 12, 2018, vol. 154, No. 2, pp. 266-273.

Ku Y-Y et al: "An efficient synthesis of DES-N-methyl-N-acetyl erythromycin derivatives via the N-oxide", Bioorganic & Medicinal Chemistry Letters, Elsevier, Amsterdam, NL, vol. 7, No. 9, May 6, 1997 (May 6, 1997), pp. 1203-1206, XP004136215, ISSN: 0960-894X, DOI: 10.1016/S0960-894X(97)00195-9 * p. 1204.

Daenas, European Journal of Pharmacology 553 (2006) 280-287. (Year: 2006).

Pfizer, Zithromax product page, Jan. 2013. (Year: 2013).

Murtaza, Biomed Res Int. 2014; 2014:145342. (Year: 2014).

Llovet, N Engl. J Med 359: 4 Jul. 24, 2008. (Year: 2008).

Ozsvari, Aging 2018, vol. 10, No. 2, Feb. 19, 2018. (Year: 2018).

Medline Plus, Tetracycline, Aug. 15, 2017, https://medlineplus.gov/druginfo/meds/a682098.html. (Year: 2017).

Schönfeld peter et al: "Short- and medium-chain fatty acids in energy metabolism: the cellular perspective", Journal of Lipid Research, vol. 57, No. 6, Jun. 1, 2016 (Jun. 1, 2016), pp. 943-954, XP055929058.

Sfogliarini Chiara et al: "Tamoxifen Twists Again: On and Off-Targets in Macrophages and Infections", Frontiers in Pharmacology, vol. 13, Mar. 30, 2022 (Mar. 30, 2022), pp. 1-8, XP093039344.

Liu, Chinese Medical Journal, Jun. 20, 2016, vol. 129, Issue 12. (Year: 2016).

KR20030082200A, published 2002, machine translation. (Year: 2002).

Jung, International Immunopharmacology 26 (2015) 432-438. (Year: 2015).

Hang Howard C. et al: "Exploring Protein Lipidation with Chemical Biology", Chemical Reviews, vol. 111, No. 10, Sep. 16, 2011 (Sep. 16. 2011), pp. 6341-6358, XP093075617, US ISSN: 0009-2665, DOI: 10.1021/cr2001977.

AZITHROMYCIN AND ROXITHROMYCIN DERIVTIVES AS SENOLYTIC DRUGS

This application is a divisional of U.S. application Ser. No. 17/282,212, filed Apr. 1, 2021 which is the U.S. national phase of International Application No. PCT/US2019/054231 filed Oct. 2, 2019 which designated the U.S. and claims priority to U.S. Provisional Application No. 62/740,137 filed Oct. 2, 2018, U.S. Provisional Application No. 62/750,559 filed Oct. 25, 2018 and U.S. Provisional Application No. 62/788,187 filed Jan. 4, 2019, the entire contents of each of which are hereby incorporated by reference.

FIELD

The present disclosure relates to senolytic drugs, compounds that selectively induce death in senescent cells.

BACKGROUND

As a diversity of organisms undergo chronological aging, many genetic, phenotypic and metabolic defects accumulate. The accumulation includes the onset of senescence in a variety of cell types. The overall view of accumulated defects is consistent with the "accumulated damage" hypothesis of aging.

Senescence is a clear hallmark of normal chronological aging. Senescence involves potentially irreversible cell cycle arrest, via the induction of CDK-inhibitors, such as p16-INK4A, p19-ARF, p21-WAF and p27-KIP1, as well as the onset of SASP (senescence-associated secretory phenotype), and the induction of key lysosomal enzymes (Beta-Galactosidase) and Lipofuscin, an established aging-pigment. Interestingly, SASP results in the secretion of a wide array of inflammatory cytokines, such as IL-1-beta and IL-6, allowing senescent cells to "contagiously" spread the senescence phenotype from one cell type to another, systemically throughout the body, via chronic inflammation. Such chronic inflammation can also promote the onset of cancer, as well as drive tumor recurrence and metastasis.

Using the promoter of p16-IN4KA as a transgenic probe to detect and mark senescent cells, several research groups have now created murine models of aging in which senescent cells can be genetically eliminated in a real-time temporal fashion. Although this cannot be used as an anti-aging therapy, it can give us an indication whether the removal of senescent cells can potentially have therapeutic benefits to the organism. Results to date show great promise, indicating that the genetic removal of senescent cells can indeed prolong health span and lifespan.

As a consequence of this genetic data, a large number of pharmaceutical companies are actively engaged in the discovery of "senolytic" drugs that can target senescent cells. In theory, such senolytic drugs would have the potential to undue various effects related to aging. However, drug development is a lengthy and expensive process, requiring extensive clinical trials and having the risk of failing for one of many potential reasons.

What is needed, then, is the identification of compounds already approved for one or more treatments that also have senolytic activity.

BRIEF SUMMARY

This disclosure relates compounds having senolytic activity that may be used as senolytic drugs. Many FDA-approved drugs possess varying degrees of senolytic activity. Identifying such compounds and improving their selectivity towards inhibiting senescent cells would dramatically accelerate their availability for anti-aging drug trials. Described herein are the identification of such compounds, identified following the use of controlled DNA-damage as a tool to induce senescence in human fibroblasts. BrdU-treatment, which has a long history of being used as a DNA-damaging agent, may be used as an efficient platform for screening compounds for senolytic activity. More specifically, BrdU-treatment allows for reproducibly inducing senescence in cultured cells, with high efficiency.

Using the BrdU-treatment as a platform for identifying senolytic activity, the inventors identified two macrolide antibiotics of the erythromycin family, specifically azithromycin and roxithromycin, as clinically-approved drugs that have efficacy as senolytic drugs. In direct support of the high specificity of these complex interactions, the parent macrolide compound—erythromycin itself—has no senolytic activity in the screening assay disclosed herein. However, telithromycin (another macrolide), also shows senolytic activity, as do chemical analogs or derivatives of azithromycin, roxithromycin, and telithromycin. Note that this description uses the terms 'derivative' and 'analog' interchangeably. The screening methodology has been used to identify senolytic agents, such as those described herein. Further, senolytic agents may be modified with one or more targeting signals to improve senolytic activity, and may be used in conjunction with other therapeutic agents, such as mitochondrial biogenesis inhibitors, to more potently eradicate senescent cells.

The present approach may take various forms. Some embodiments may take the form of a senolytic composition having a therapeutic amount of at least one senolytic agent selected from azithromycin, roxithromycin, telithromycin, an azithromycin analog, a roxithromycin analog, and a telithromycin analog. This disclosure uses the terms "derivative" and "analog" interchangeably, although the typical usage may be different. For example, embodiments may be in the form of a pharmaceutically effective amount of a formula selected from one of the following:

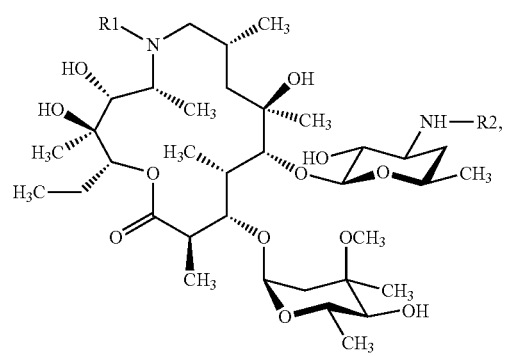

-continued

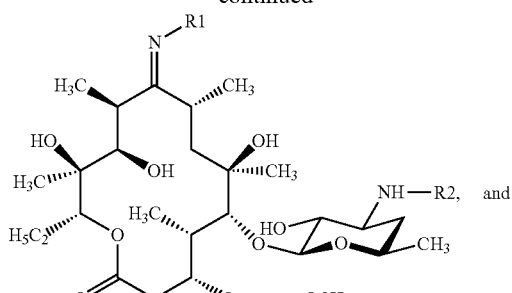

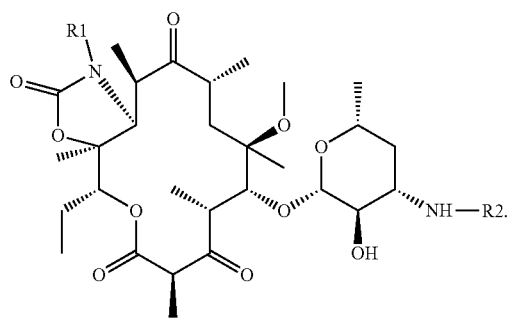

In such embodiments, R1 and R2 represent functional groups, may be the same group or different groups, provided that at least one of R1 and R2 is one of a membrane-targeting signal and a mitochondria-targeting signal. Otherwise, R1 and R2 are selected from hydrogen, carboxyl, an alkane, a cyclic alkane, an alkane-based derivative, an alkene, a cyclic alkene, an alkene-based derivative, an alkyne, an alkyne-based derivative, a ketone, a ketone-based derivative, an aldehyde, an aldehyde-based derivative, a carboxylic acid, a carboxylic acid-based derivative, an ether, an ether-based derivative, an ester, an ester-based derivative, an amine, an amine-based derivative, an amide, an amide-based derivative, a monocyclic arene, a polycyclic arene, a heteroarene, an arene-based derivative, a heteroarene-based derivative, a phenol, a phenol-based derivative, a benzoic acid, and a benzoic acid-based derivative. In some embodiments, at least one of R1 and R2 is a membrane-targeting signal selected from palmitic acid, stearic acid, myristic acid, oleic acid, a short-chain fatty acid, and a medium-chain fatty acid. The senolytic composition of claim 1, wherein at least one of R1 and R2 is a mitochondria-targeting signal selected from tri-phenyl-phosphonium (TPP), a TPP-derivative, guanidinium, a guanidinium derivative, and 10-N-nonyl acridine orange. In some embodiments of the senolytic composition, at least one of R1 and R2 is a TPP-derivative selected from 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP.

In some embodiments, the senolytic compound may be an azithromycin derivative or analog. For example, the senolytic composition may be a compound having the formula

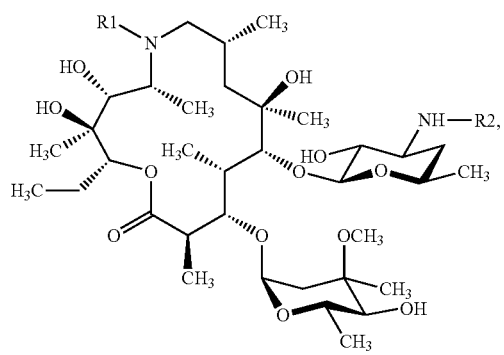

wherein either R1 is methyl and R2 is one of a membrane-targeting signal and a mitochondria-targeting signal, or R1 is one of a membrane-targeting signal and a mitochondria-targeting signal and NH-R2 is $N(CH_3)_2$. Of course, the functional groups may be different, as described elsewhere herein. Under the typical usage of the terminology, a single substitution from the base compound (e.g., azithromycin) would be referred to as an analog, and one or more modifications made to a base compound may be considered a derivative. For simplicity, this disclosure uses the terms "analog" and "derivative" interchangeably.

In some embodiments, the senolytic compound may be a roxithromycin derivative or analog. For example, the senolytic composition may be a compound having the formula

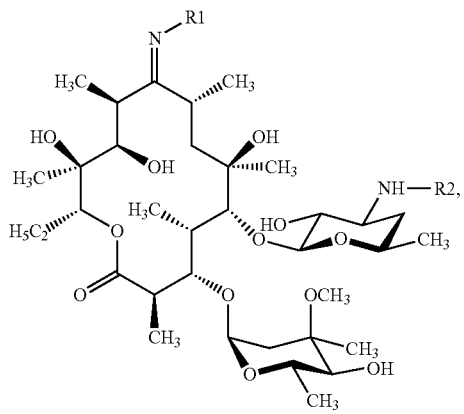

wherein either R1 is O—$CH_2$—O—$(CH_2)_2$—$OCH_3$ and R2 is one of a membrane-targeting signal and a mitochondria-targeting signal, or R1 is one of a membrane-targeting signal and a mitochondria-targeting signal and NH—R2 is $N(CH_3)_2$. Of course, the functional groups may be different, as described elsewhere herein.

In some embodiments, the senolytic compound may be a telithromycin derivative or analog. For example, the senolytic composition may be a compound having the formula

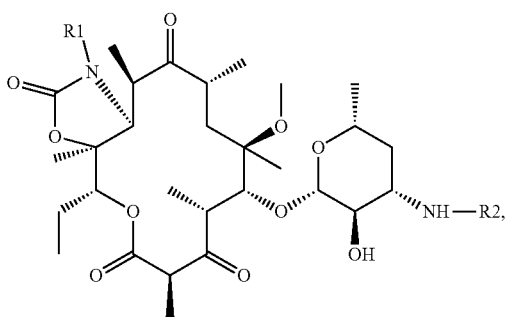

wherein either R1 is

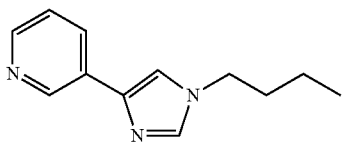

and R2 is one of a membrane-targeting signal and a mitochondria-targeting signal, or R1 is one of a membrane-targeting signal and a mitochondria-targeting signal and NH—R2 is $N(CH_3)_2$.

In preferred embodiments of the present approach, the senolytic composition has at least one functional group targeting signal to improve the mitochondrial uptake and, as a result, the senolytic activity of the compound. Using the generic formula described above, at least one of R1 and R2 is either a membrane-targeting signal selected from palmitic acid, stearic acid, myristic acid, oleic acid, a short-chain fatty acid, and a medium-chain fatty acid, or a mitochondria-targeting signal selected from 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP.

In some embodiments, the senolytic composition may also include one or more additional therapeutic agents. For example, some embodiments may include a therapeutic amount of at least one of tetracycline, chlortetracycline, oxytetracycline, demeclocycline, methacycline, doxycycline, minocycline, and tigecycline. Some embodiments may include a therapeutic amount of at least one of pyrvinium, atovaquone, bedaquiline, irinotecan, sorafenib, niclosamide, stirpentol, chloroquine, and rapamycin. And some embodiments may include a therapeutic amount of at least one of a mitoriboscin, a mitoketoscin, a mitoflavoscin, 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP. It should be appreciated that a TPP-derivative may be conjugated with a derivative or analog of a senolytic compound, and function as a targeting signal, and may be present as separate therapeutic compound. Some embodiments may include at least one of Vitamin C, berberine, caffeic acid phenyl ester, silibinin, brutieridin, and melitidin.

Embodiments taking the form of the senolytic composition may be made in various forms, including, for example, a cosmetic, a pill, a lotion, a shampoo, a cream, a soap, a skin cleaner, a shaving preparation, an after-shave, a gel, a stick, a paste, a spray, an aerosol, a powder, a liquid, an aqueous suspension, an aqueous solution, a foam, a transdermal patch, a tincture, and a vapor. These forms are intended to be non-limiting examples.

Embodiments of the present approach may take the form of a composition for use in senescence therapy. Such compositions include a therapeutic amount of a senolytic agent as discussed above. For example, the senolytic agent may be one of an azithromycin analog, a roxithromycin analog, and a telithromycin analog, having at least one of (i) a membrane-targeting signal selected from palmitic acid, stearic acid, myristic acid, oleic acid, a short-chain fatty acid, and a medium-chain fatty acid; and (ii) a mitochondria targeting signal selected from tri-phenyl-phosphonium (TPP), a TPP-derivative, guanidinium, guanidinium derivatives, and 10-N-nonyl acridine orange.

In some embodiments, the composition for use in senescence therapy may also include a therapeutic amount of at least one of tetracycline, chlortetracycline, oxytetracycline, demeclocycline, methacycline, doxycycline, minocycline, and tigecycline. Some embodiments may include a therapeutic amount of at least one of pyrvinium, atovaquone, bedaquiline, irinotecan, sorafenib, niclosamide, stirpentol, chloroquine, and rapamycin. And some embodiments may include a therapeutic amount of at least one of a mitoriboscin, a mitoketoscin, a mitoflavoscin, 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP. Additionally, some embodiments may include at least one of Vitamin C, berberine, caffeic acid phenyl ester, silibinin, brutieridin, and melitidin.

The present approach may take the form of a method for inducing death of senescent cells in a subject. In such embodiments, a therapeutic amount of a senolytic agent is administered to the subject. The senolytic agent may be at least one of azithromycin, roxithromycin, telithromycin, an azithromycin analog, a roxithromycin analog, and a telithromycin analog, as discussed above. Derivatives or analogs may include one or more targeting signals, such as a membrane-targeting and a mitochondria targeting signal. The method may include administering one or more additional therapeutic agents. For example, a therapeutic amount of at least one of tetracycline, chlortetracycline, oxytetracycline, demeclocycline, methacycline, doxycycline, minocycline, and tigecycline may be administered with the senolytic agent. As another example, therapeutic amount of at least one of pyrvinium, atovaquone, bedaquiline, irinotecan, sorafenib, niclosamide, stirpentol, chloroquine, and rapamycin may be administered. As a further example, a therapeutic amount of at least one of a mitoriboscin, a mitoketoscin, a mitoflavoscin, 2-butene-1,4-bis-TPP; a derivative of 2-butene-1,4-bis-TPP; 2-chlorobenzyl-TPP; a derivative of 2-chlorobenzyl-TPP; 3-methylbenzyl-TPP; a derivative of 3-methylbenzyl-TPP; 2,4-dichlorobenzyl-TPP; a derivative of 2,4-dichlorobenzyl-TPP; 1-naphthylmethyl-TPP; a derivative of 1-naphthylmethyl-TPP; p-xylylenebis-TPP; and a derivative of p-xylylenebis-TPP may be administered. As another example, a therapeutic amount of at least one of Vitamin C, berberine, caffeic acid phenyl ester, silibinin, brutieridin, and melitidin may be administered. The therapeutic agent may be co-administered with the senolytic agent, or in some embodiments may be administered before or after the senolytic agent.

Some embodiments of the present approach may take the form of a method for delaying the onset of an age-related disease in a subject. The age-related disease may be at least one of atherosclerosis, arthritis, cancer, cardiovascular disease, cataract, dementia, diabetes, hair loss, hypertension, inflammatory disease, kidney disease, muscular atrophy, neurological disease, osteoarthritis, osteoporosis, pulmonary disease, vertebral disc degeneration, and alopecia. For example, the age-related disease may be a neurological disease, such as mild cognitive impairment, motor neuron dysfunction, Alzheimer's disease, Parkinson's disease, and macular degeneration. In such embodiments, a therapeutic amount of a senolytic agent, as described, herein may be administered to the subject. In some embodiments, the senolytic agent may be administered with another therapeutic agent, as described herein. The senolytic agent may be administered at the onset, i.e., at or shortly after the diagnosis of an age-related disease. Alternatively, the senolytic agent may be administered routinely after diagnosis, and the frequency and dosage may be determined using techniques known in the art. In some embodiments, the senolytic agent may be administered prior to onset, particularly where an age-related disease is expected or likely to occur in a subject (e.g., due to genetic markers or other biological markers).

The present approach may also take the form of a composition for use in delaying the onset of an age-related disease. For example, and without limitation, the present approach may be used to delay the onset of atherosclerosis, arthritis, cancer, cardiovascular disease, cataract, dementia, diabetes, hair loss, hypertension, inflammatory disease, kidney disease, muscular atrophy, neurological disease, osteoarthritis, osteoporosis, pulmonary disease, vertebral disc degeneration, and alopecia. In such embodiments, a therapeutic amount of a senolytic agent comprising at least one of azithromycin, roxithromycin, telithromycin, an azithromycin analog, a roxithromycin analog, and a telithromycin analog, may be administered, as described herein. In some embodiments, the senolytic agent may be administered with another therapeutic agent, as described herein.

The present approach may also take the form of a method for screening compounds for senolytic activity. In such embodiments, a cell population is exposed to a DNA damaging agent for a first duration to generate a senescent cell population. An example DNA damaging agent is bromodeoxyuridine (BrdU), though other DNA damaging agents may be used without departing from the present approach. At least a portion of the senescent cell population is treated with a candidate compound for a second duration to form a treated cell population. Candidate compounds are the compounds being screened for senolytic activity. The treated cell population is analyzed for at least one marker of senolytic activity. Example markers of senolytic activity include cell viability, aerobic glycolysis, autophagy, inhibitory activity, and cell proliferation reduction. For example, autophagic LC3 proteins may be quantitatively measured, as described herein. The Sulphorhodamine B assay and measuring cell-induced electrical impedance are examples of assays that may be used to analyze cell populations for senolytic activity. The first duration may vary, and in the embodiments described below, was about 8 days. The second duration may also vary, and in the embodiments discussed below was about 3 days to about 5 days. In some embodiments, the BrdU may be washed out before the second duration.

Further embodiments of the present approach may be recognized by those having ordinary skill in the art, having reviewed the following detailed description.

DESCRIPTION

The following description includes the currently contemplated modes of carrying out exemplary embodiments of the present approach. The following description is not to be taken in a limiting sense, and is made merely for the purpose of illustrating the general principles of the invention.

Figure 1:
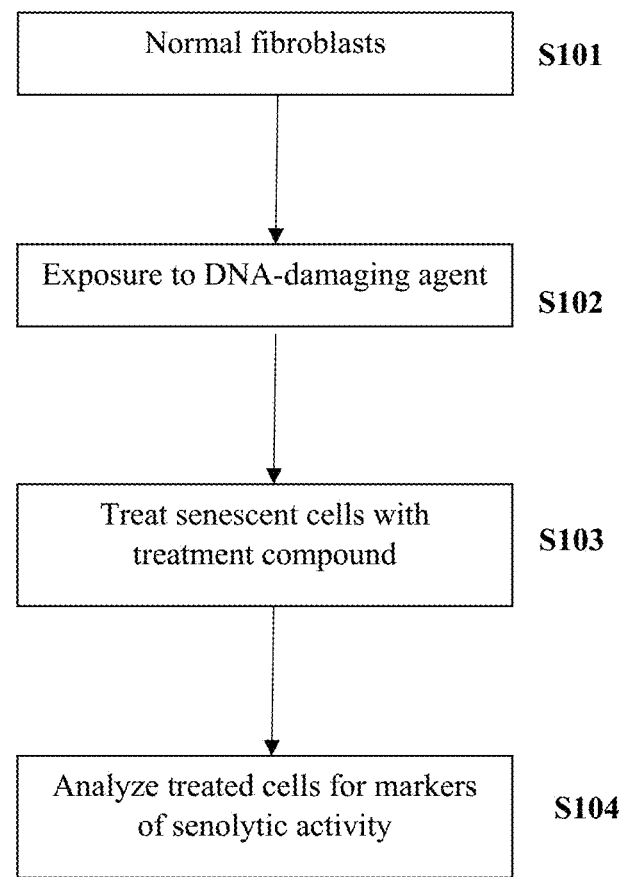
FIG. 1 illustrates a method for screening and identifying senolytic drugs according to an embodiment of the present approach.

As described herein, the present approach relates to the development of a screening assay for inducing senescence, and its use to identify compounds having senolytic activity, i.e., selective inhibition of, and induction of death in, senescent cells. The present approach may, in some embodiments, be used to identify and repurpose clinically-approved therapeutics with senolytic activity for the treatment of aging and aging-associated disorders. FIG. 1 illustrates a screening methodology according to the present approach. At step S101, normal fibroblasts are selected. Next, at step S102, the cells are exposed to a DNA-damaging agent to induce senescence. For example, bromodeoxyuridine may be used as the damaging agent. The senescent cells are treated with a candidate treatment compound at step S103. Of course, multiple candidate treatment compounds may be screened using portions of the senescent cells, and variations in compound concentration and treatment duration may be included in this step. Finally, at step S104, treated cells are analyzed for markers of senolytic activity. Normal cells and/or untreated senescent cells may also be analyzed, as controls. Senolytic activity markers used may vary, and may include, for example, cell viability, aerobic glycolysis, autophagy, inhibitory activity, and cell proliferation reduction.

Bromodeoxyuridine (5-bromo-2'-deoxyuridine), also known as BrdU, may be used to induce senescence. BrdU is an analog of the nucleoside thymidine commonly used to identify proliferating cells. BrdU induces controlled DNA damage, and drives cells towards senescence with high efficiency. The BrdU assay of the present approach calls for subjecting normal fibroblasts to prolonged culture (8-days) in the presence of BrdU at 100 µM to induce controlled DNA-damage and senescence. In demonstrative embodiments, the inventors used two independent normal, non-immortalized, human fibroblast cell lines, MRC-5 lung cells (for screening) and BJ skin cells (for validation), in the BrdU-based assay. Then, isogenically-matched cultures of normal and senescent fibroblasts may be used for drug screening to identify drugs having senolytic activity. Senolytic activity may be detected using the sulforhodamine B assay, also known in the art as the SRB assay. This assay measures the amount of protein remaining attached to the tissue-culture dishes, and is a surrogate marker for cell viability. This approach may be used to rapidly screen compounds, including clinically-approved drugs, such as, for example, antibiotics. For example, in embodiments described herein, the present approach was used to screen erythromycin family members, including azithromycin and roxithromycin, among other compounds. It should be appreciated that the present approach may be used to screen other compounds.

Mechanistically, the present approach directly compares the responses of "normal" fibroblasts and "senescent" fibroblasts, side-by-side. Drugs that preferentially killed senescent fibroblasts, but not normal fibroblasts, may be considered positive for senolytic activity. Using this approach in the embodiments discussed herein, the inventors identified two erythromycin-family members, azithromycin and roxithromycin that preferentially targeted senescent fibroblasts. Table 1, below, shows the results for erythromycin, azithromycin, and roxithromycin, at two concentrations, and shows that azithromycin and roxithromycin have senolytic activity at 100 µM. Telithromycin, another macrolide, also showed beneficial senolytic activity, as well as chemical analogs of azithromycin, roxithromycin, and telithromycin. However, erythromycin itself did not show any senolytic activity.

TABLE 1

Results for senolytic activity screening for erythromycin-family antibiotics.

|  | Viability of senescent MRC-5 cells (% versus control) | |
|---|---|---|
|  | 100 µM | 50 µM |
| Erythromycin | 100 | 100 |
| Azithromycin | 56.01 | 100 |
| Roxithromycin | 30.99 | 100 |

The precise chemical structures of some of the erythromycin family members screened in the disclosed embodiments are shown below as compounds I-IV. Note that the structures of the compounds in the erythromycin family have significant similarities, but senolytic activity exists in azithromycin, roxithromycin, and telithromycin.

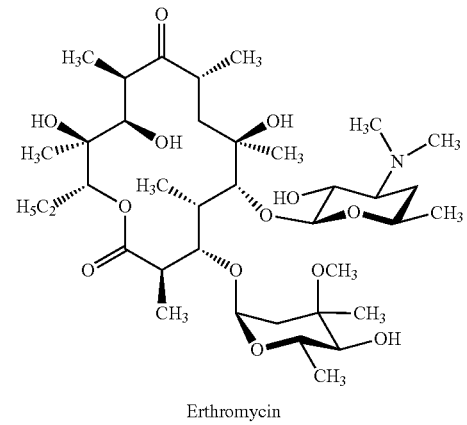

Erthromycin (I)

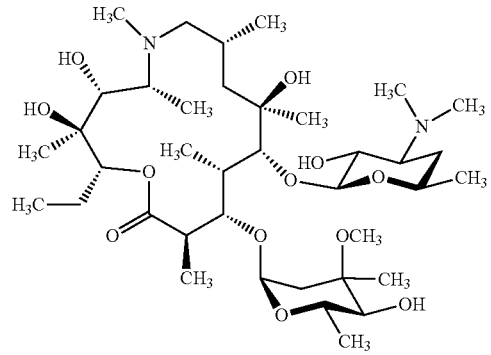

Azithromycin (II)

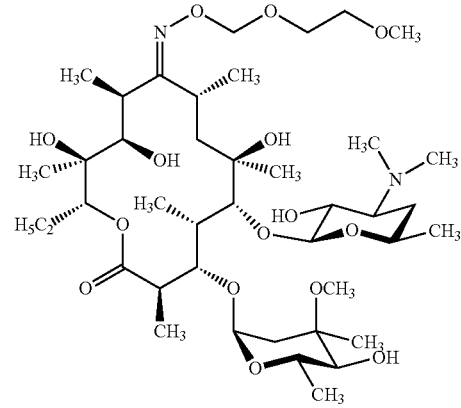

Roxithromycin (III)

-continued (IV)

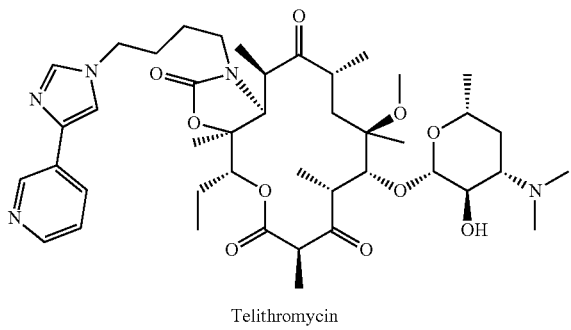

Telithromycin

Figure 2:
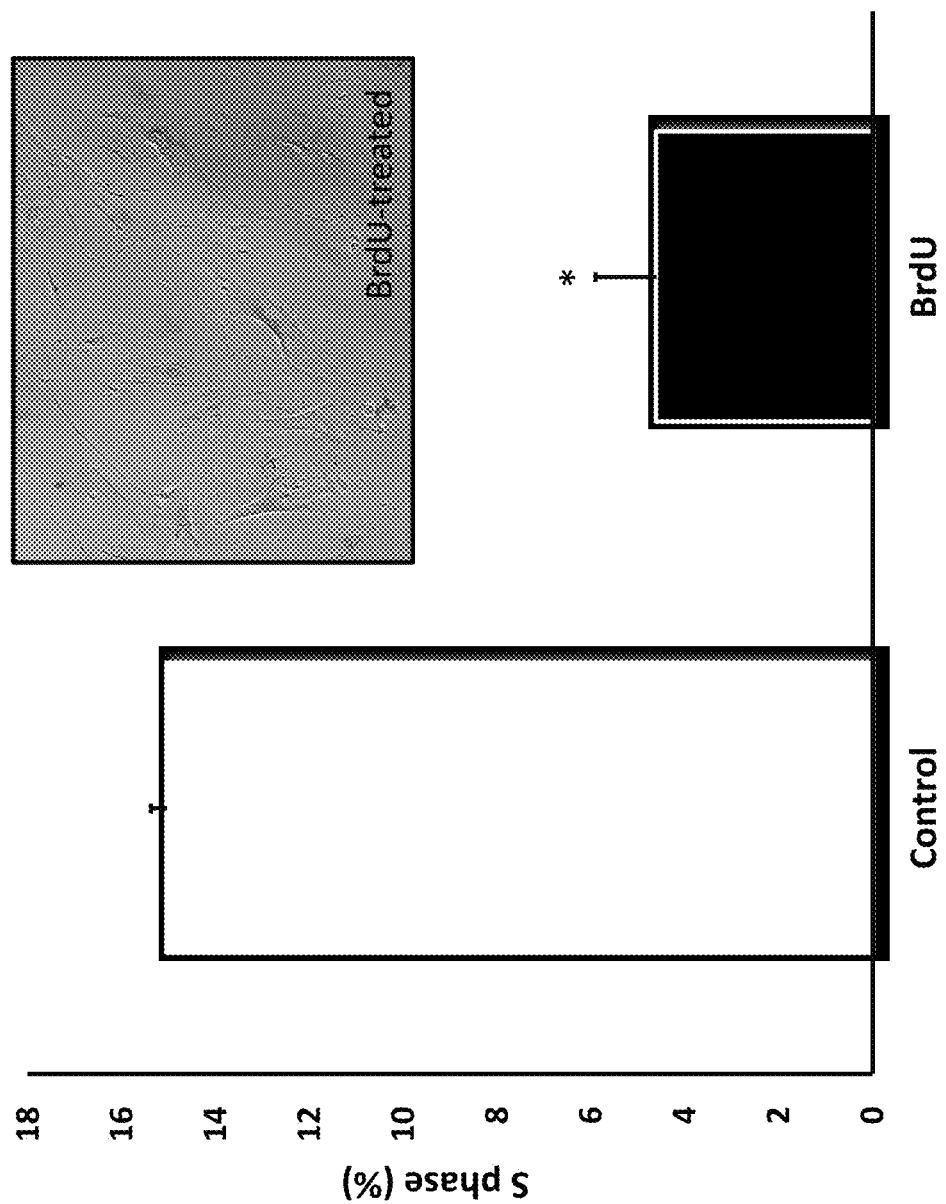
FIG. 2 shows results of DNA synthesis reduction in MRC-5 fibroblasts.

Furthermore, the inventors validated the use of BrdU-induced DNA-damage as being sufficient to induce cellular senescence. FIG. 2 shows results of DNA synthesis reduction in MRC-5 fibroblasts. Two-day treatment with BrdU significantly reduced DNA synthesis in MRC-5 fibroblasts by ~70%, as measured with the Muse cell cycle kit. MRC-5 cells after 8 days of BrdU treatment were positively stained for beta-galactosidase, a biomarker of cellular senescence. For this data, n=3; and * indicates p<0.05. The inlay in FIG. 2 shows beta-galactosidase positivity in the cells treated with BrdU. The results evidence that the cells treated with BrdU underwent cell cycle arrest, as evidenced by both a ~70% reduction in the number of cells in S-phase, and the induction of beta-galactosidase activity. These results confirm that BrdU-treatment of MRC-5 cells effectively inhibits DNA-synthesis and induces beta-galactosidase, both hallmarks of senescence.

Figure 3A:
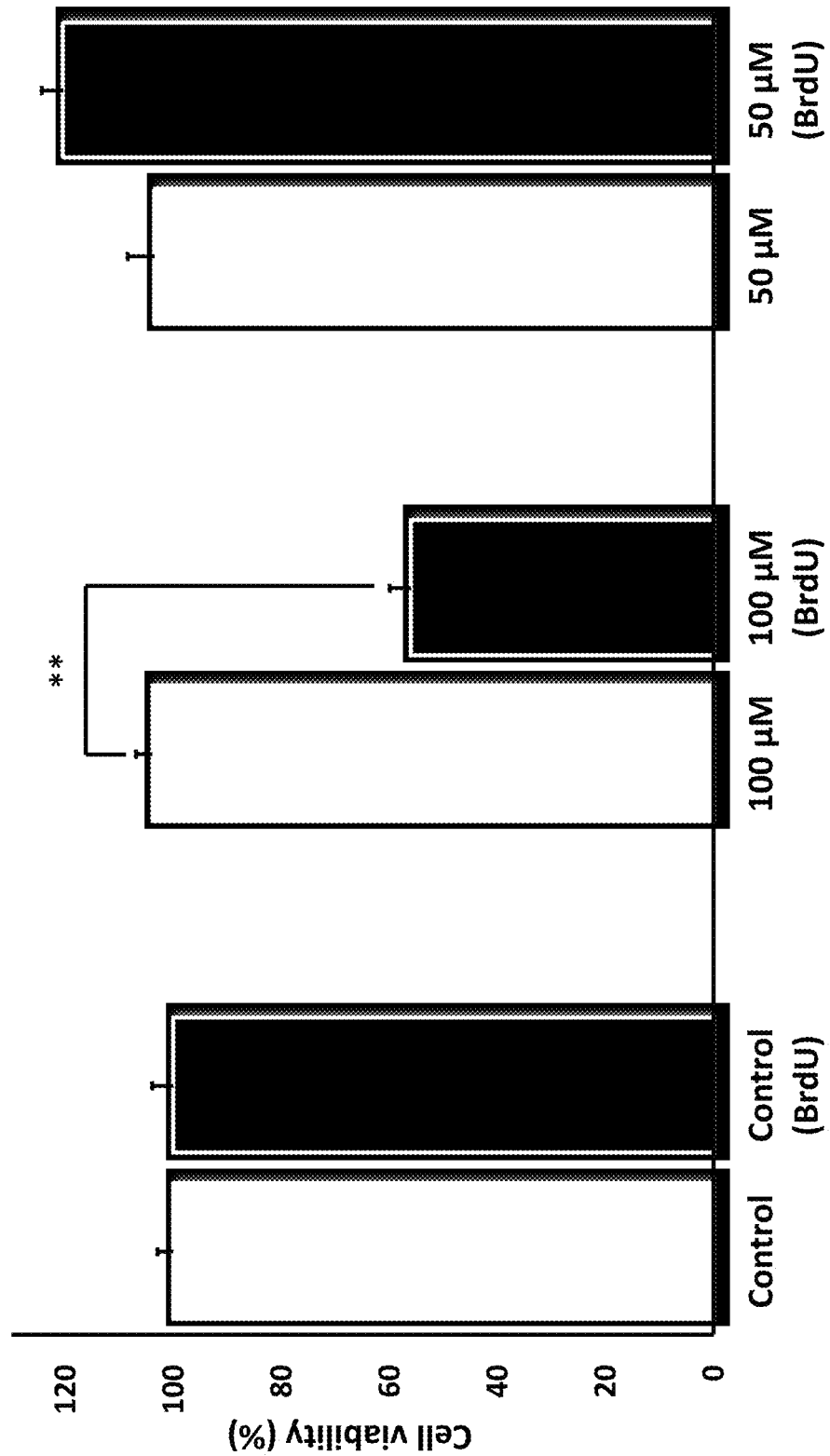
FIG. 3A shows results from the SRB assay for azithromycin in MRC-5 fibroblasts.
Figures 3B, 3C:
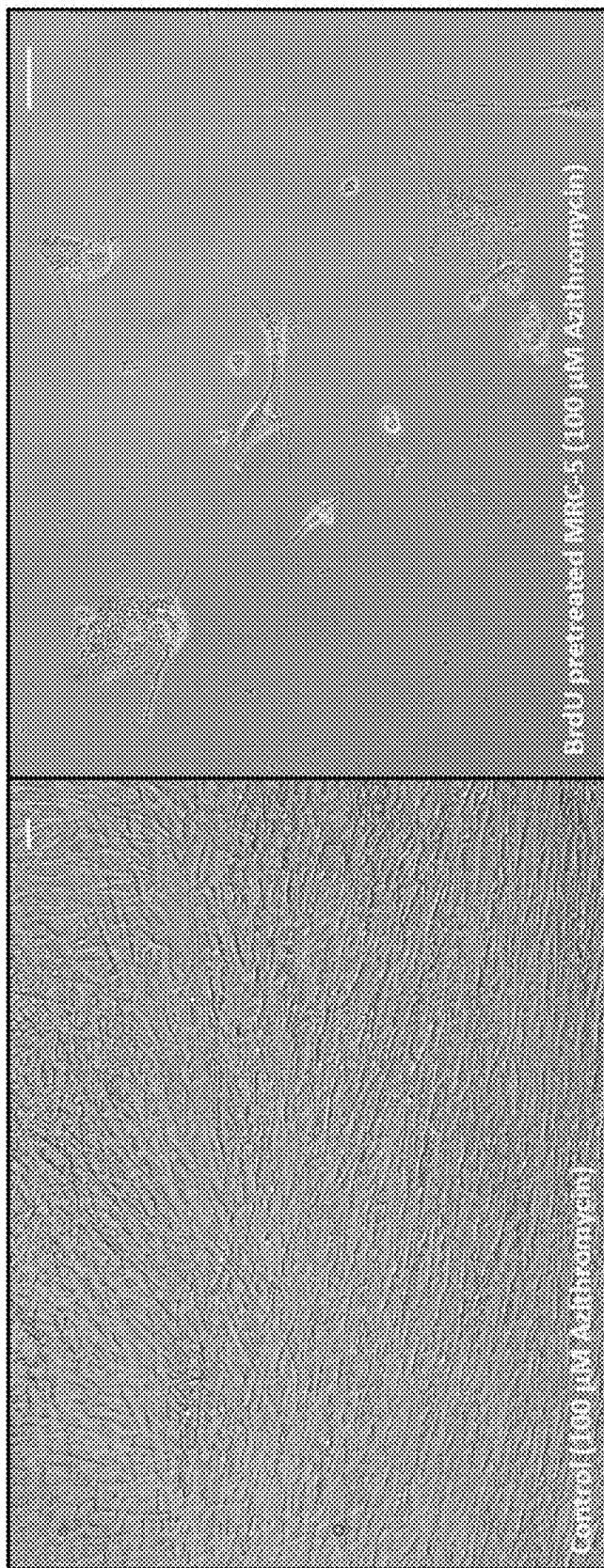
FIGS. 3B and 3C show images of MRC-5 fibroblasts treated with 100 µM azithromycin, without and with BrdU pretreatment, respectively.

In one embodiment, azithromycin showed senolytic activity in senescent MRC-5 human lung fibroblasts. MRC-5 cells were pre-treated with BrdU for 8 days (to induce senescence), before BrdU wash out and exposure to Azithromycin for another 5 days. After that, the SRB assay was performed to determine the effects of the drug on cell viability. FIG. 3A shows results from the SRB assay for BrdU-treated MRC-5 fibroblasts treated with azithromycin at concentrations of 100 µM and 50 µM, against a control (BrdU-only). Azithromycin, at 100 µM had no effect on the viability of normal MRC-5 lung fibroblasts, but selectively killed senescent MRC-5 fibroblasts. Azithromycin at this concentration potently and selectively eliminated about 50% of senescent cells without affecting control cells after 5 days. However, azithromycin had no effect at 50 µM. These experiments were repeated at least 3 times independently, with very similar results. For this data, ** indicates p<0.01. FIGS. 3B and 3C are images of MRC-5 fibroblasts treated with 100 µM azithromycin, without and with BrdU pretreatment, respectively. These images show that azithromycin had little effect on the normal cells, but induced cell death in senescent cells. The scale bar in the upper-right of FIGS. 3B and 3C represents 20 µm.

Figure 4:
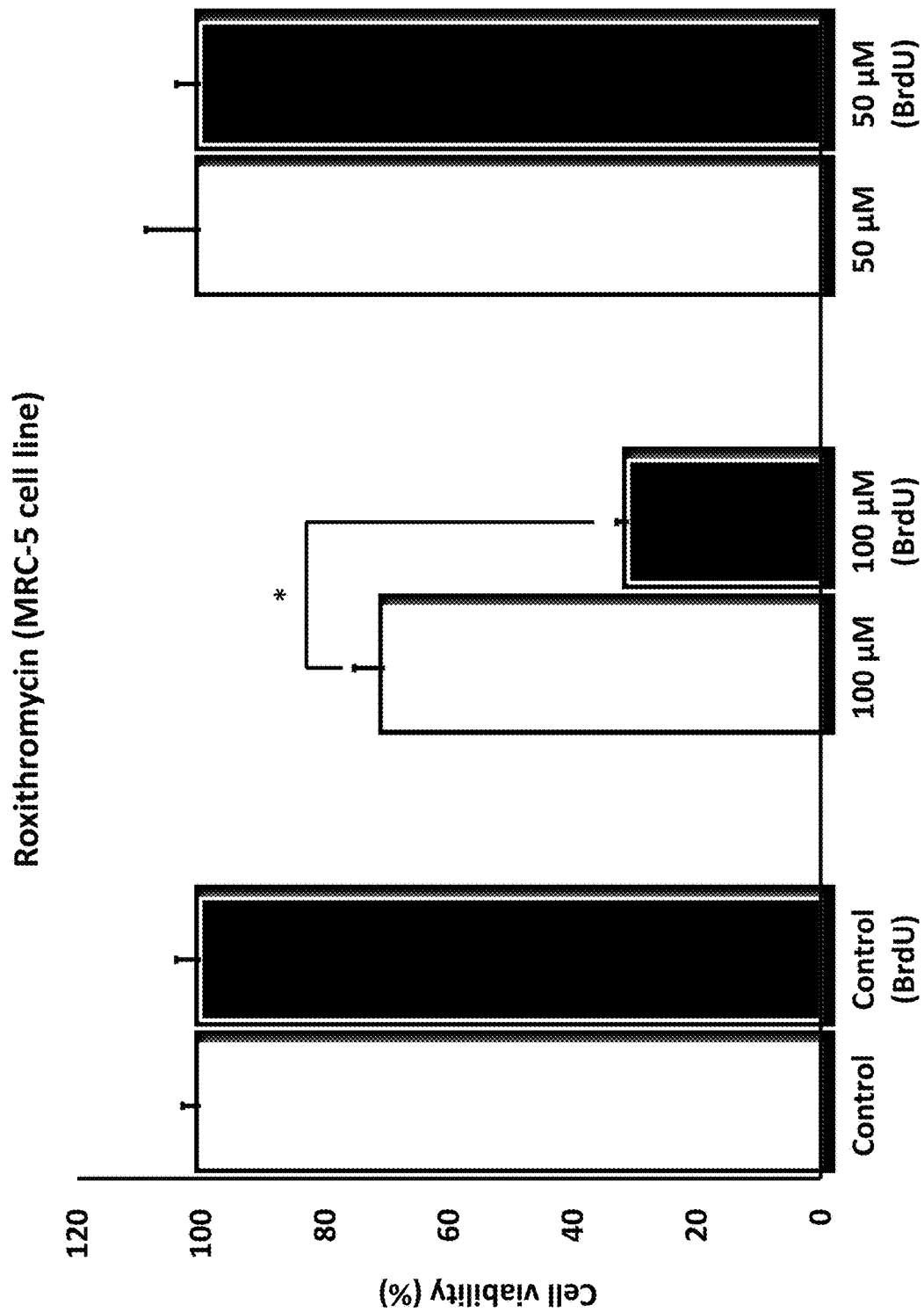
FIG. 4 shows results from the SRB assay for roxithromycin in MRC-5 fibroblasts.

In comparison, roxithromycin at the same concentration more effectively killed senescent MRC-5 fibroblasts (~70%), but also had a small effect on the viability of normal MRC-5 fibroblasts. In one embodiment, MRC-5 cells were pre-treated with BrdU for 8 days (to induce senescence), before BrdU wash out and exposure to roxithromycin for another 5 days. After the 5-day exposure, the SRB assay was performed to determine the effects of the drug on cell viability. FIG. 4 shows results from the SRB assay on MRC-5 fibroblasts treated with roxithromycin. The data shows that roxithromycin at a concentration of 100 µM had a potent and selective effect on MRC-5 cells, as it eliminated more than 50% of senescent cells after 5 days. However, roxithromycin had no effect at a 50 µM concentration. These experiments were repeated at least 3 times independently, with very similar results. The * indicates p<0.05 in FIG. 4.

The data in FIGS. 3A and 4 show that neither azithromycin nor roxithromycin showed significant effects on senescent cell viability at 50 µM. This indicates that the senolytic effects are concentration-dependent. It should be appreciated that the person having at least an ordinary skill in the art can determine an appropriate concentration for a drug having senolytic activity, using methods known and available in the art. Based on the concentrations tested, azithromycin toxicity showed the highest specificity for selectively targeting the senescent cell phenotype.

Figure 5:
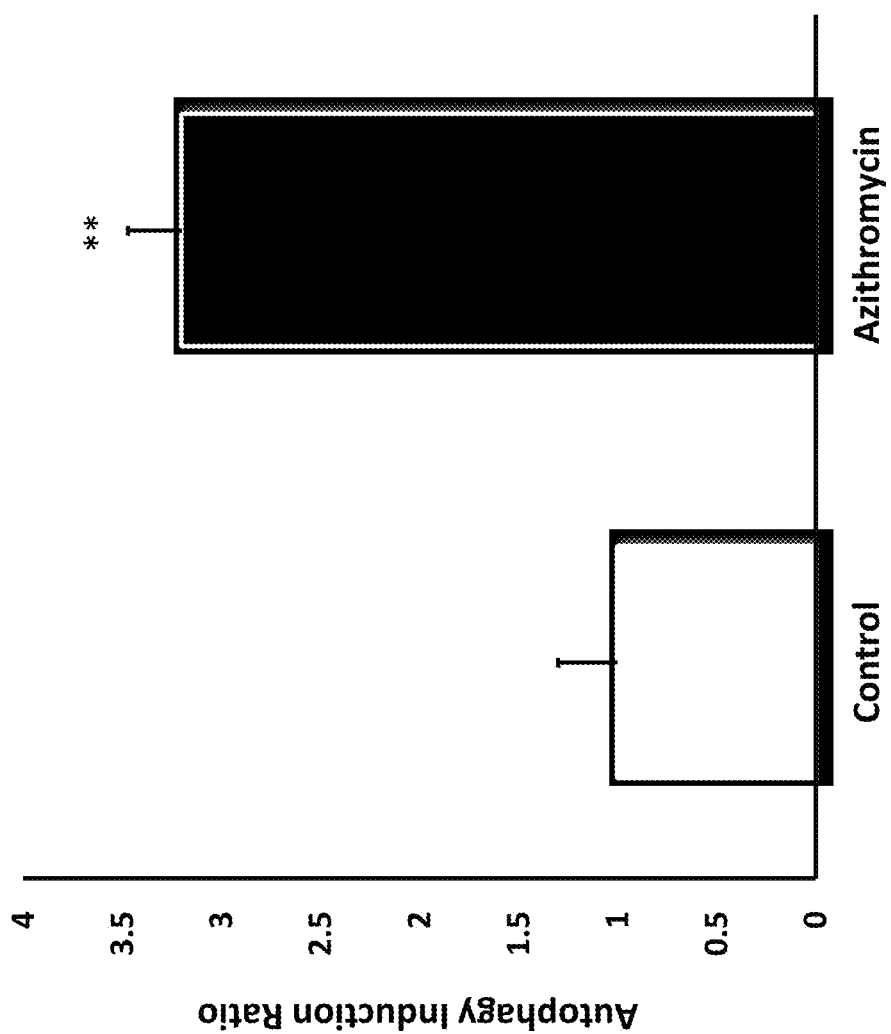
FIG. 5 shows results of autophagy induction for 50 µM azithromycin in MRC-5 fibroblasts.

Further experiments were performed using MRC-5 fibroblasts to better mechanistically understand the phenotypic and metabolic effects of azithromycin. MRC-5 cells were treated with Azithromycin at 50 µM for 72 hours. Then, autophagy was monitored by detection of autophagic LC3 proteins with the Muse Autophagy LC3-antibody based kit. FIG. 5 shows the results, and demonstrates that azithromycin is a powerful inducer of the autophagic phenotype. The ** in FIG. 5 indicates p<0.01 for this data. As shown, azithromycin treatment resulted in more than a 3-fold elevation in autophagy in MRC-5 cells.

Figure 6B:
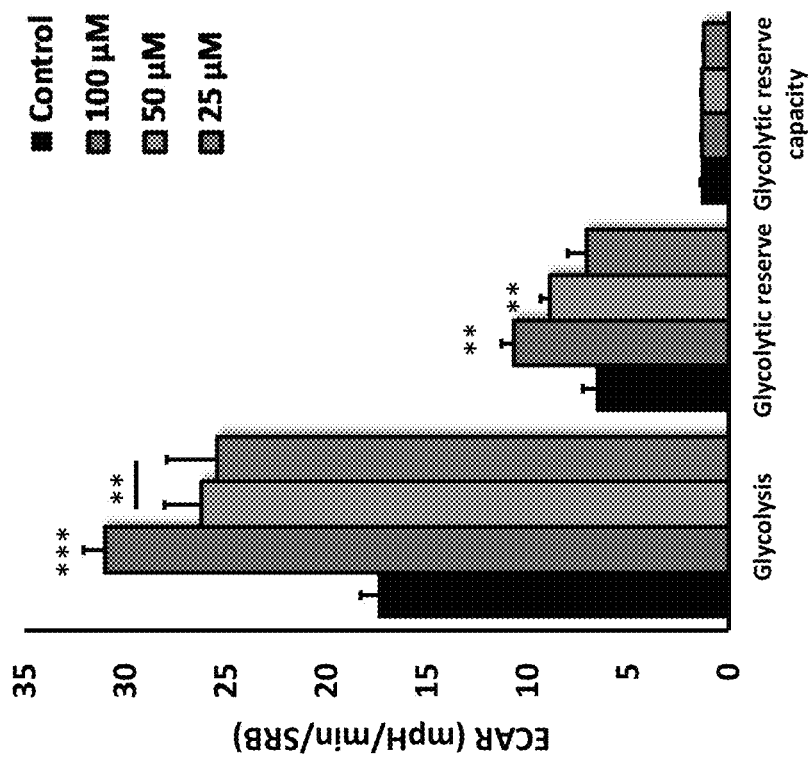
FIGS. 6A and 6B show extracellular acidification rate results from metabolic flux analysis for MRC-5 cells after 72 hours of treatment with azithromycin.
Figure 6A:
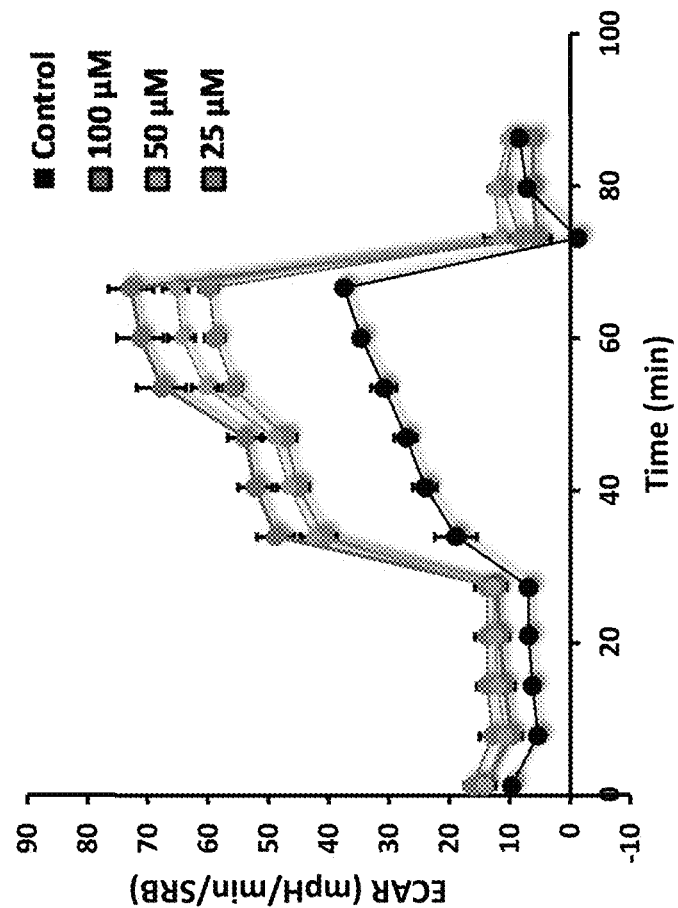

The inventors next measured the effects of azithromycin on aerobic glycolysis and mitochondrial metabolism, using the Seahorse XFe96 metabolic flux analyzer. After 72 hours of treatment with azithromycin at concentrations ranging from 25 µM to 100 µM. MRC-5 cells were subjected to metabolic flux analysis with the Seahorse XFe96 to measure extracellular acidification rate (ECAR). FIGS. 6A and 6B show ECAR data from this metabolic flux analysis, and as can be seen, azithromycin elevated aerobic glycolysis at all concentrations tested. The data in FIG. 6A, at 40 min and from top to bottom, represents azithromycin concentrations of 100 µM. 50 µM, 25 µM, and the control (i.e., vehicle only), respectively. In FIG. 6B, the bar data represents, from left to right, the control, 100 µM, 50 µM, and 25 µM. For this data, n=3;  indicates p<0.01, and * indicates p<0.001.

Figure 7A:
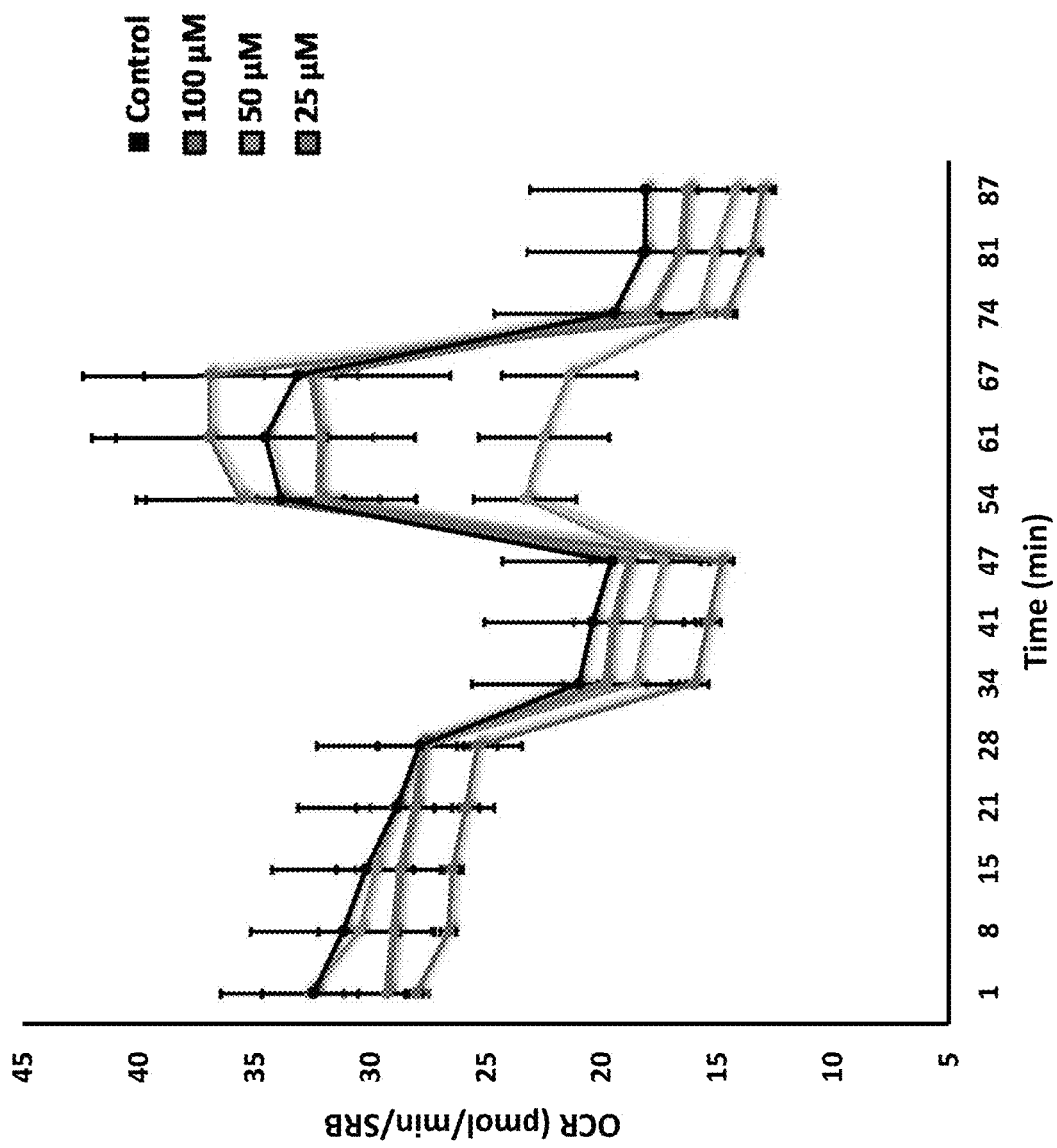
FIGS. 7A and 7B show oxygen consumption rate results from metabolic flux analysis for MRC-5 cells after 72 hours of treatment with azithromycin.

The inventors also used metabolic flux analysis to evaluate azithromycin's effects on oxygen consumption rate (OCR). The results, shown in FIGS. 7A and 7B, indicate that azithromycin has biphasic effects on OCR in MRC-5 cells. This data was generated by subjecting MRC-5 cells to metabolic flux analysis with the Seahorse XFe96, after 72 hours of treatment with azithromycin at concentrations ranging from 25 to 100 µM. From top to bottom at 41 minutes, the data in FIG. 7A lines are for the control (i.e., vehicle only), and concentrations of 25 µM, 50 µM. and 100 µM. Note that the highest azithromycin concentration, 100 µM, triggered increased mitochondrial respiration by 54 minutes, whereas the lower concentrations (50 µM) significantly reduced it. However, 25 µM did not have any significant effects on OCR. For this data, n=3, and * indicates p<0.05.

Figure 7B:
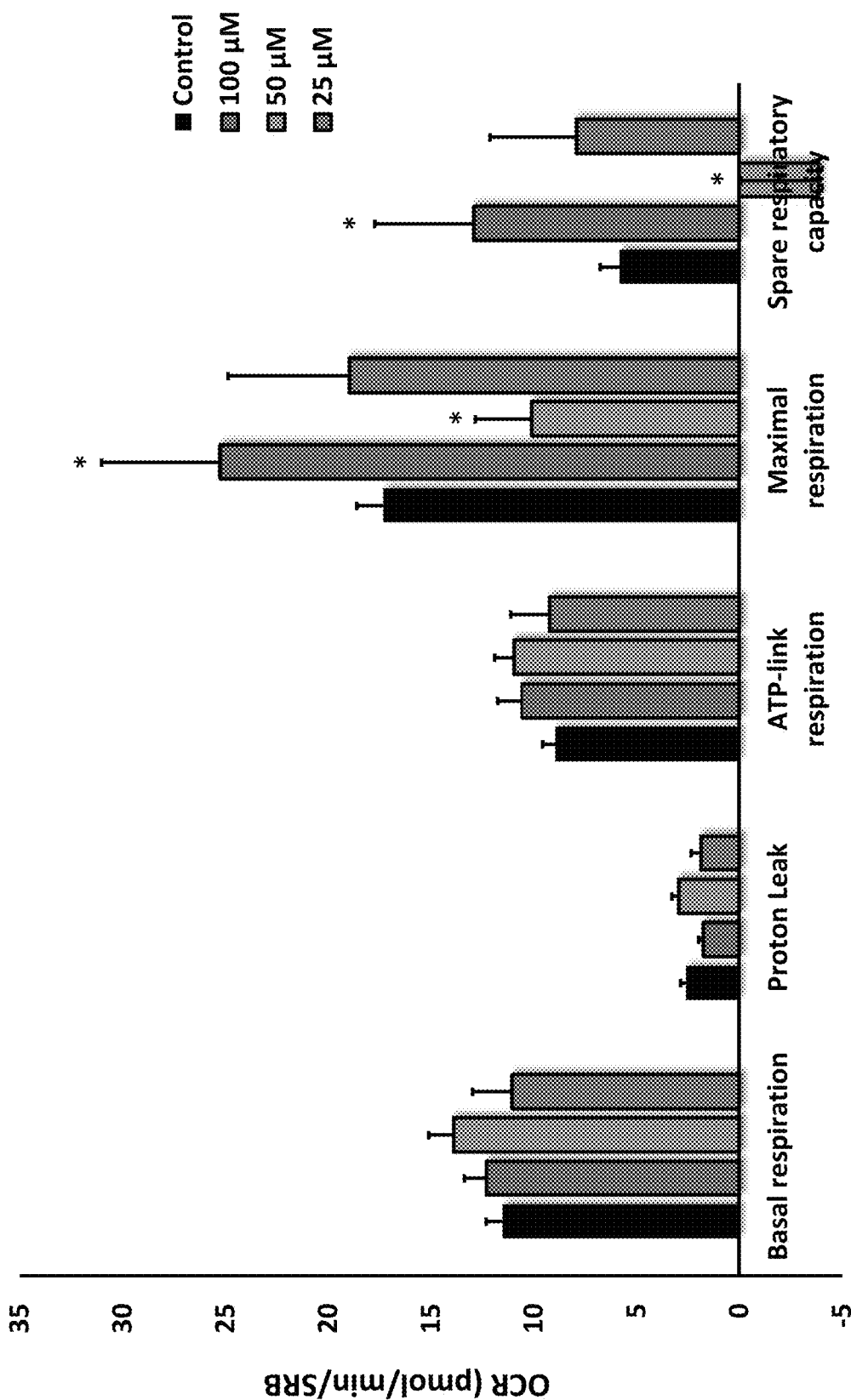

FIG. 7B shows OCR for basal respiration, proton leak, ATP-link respiration, maximal respiration, and spare respiratory capacity. From left to right, the bar data represents the control, and concentrations of 100 µM, 50 µM, and 25 µM. Note that the mitochondrial effects of azithromycin were concentration-dependent and bi-phasic. At 25 µM, azithromycin did not show significant effects on OCR. However, at 50 µM, azithromycin clearly inhibited mitochondrial metabolism, especially effecting maximal respiration and spare respiratory capacity. In contrast, at 100 µM, azithromycin stimulated maximal respiration and more than doubled spare respiratory capacity. This may represent a cellular compensatory response to azithromycin treatment, to overcome its mitochondrial inhibitory effects.

Figure 8:
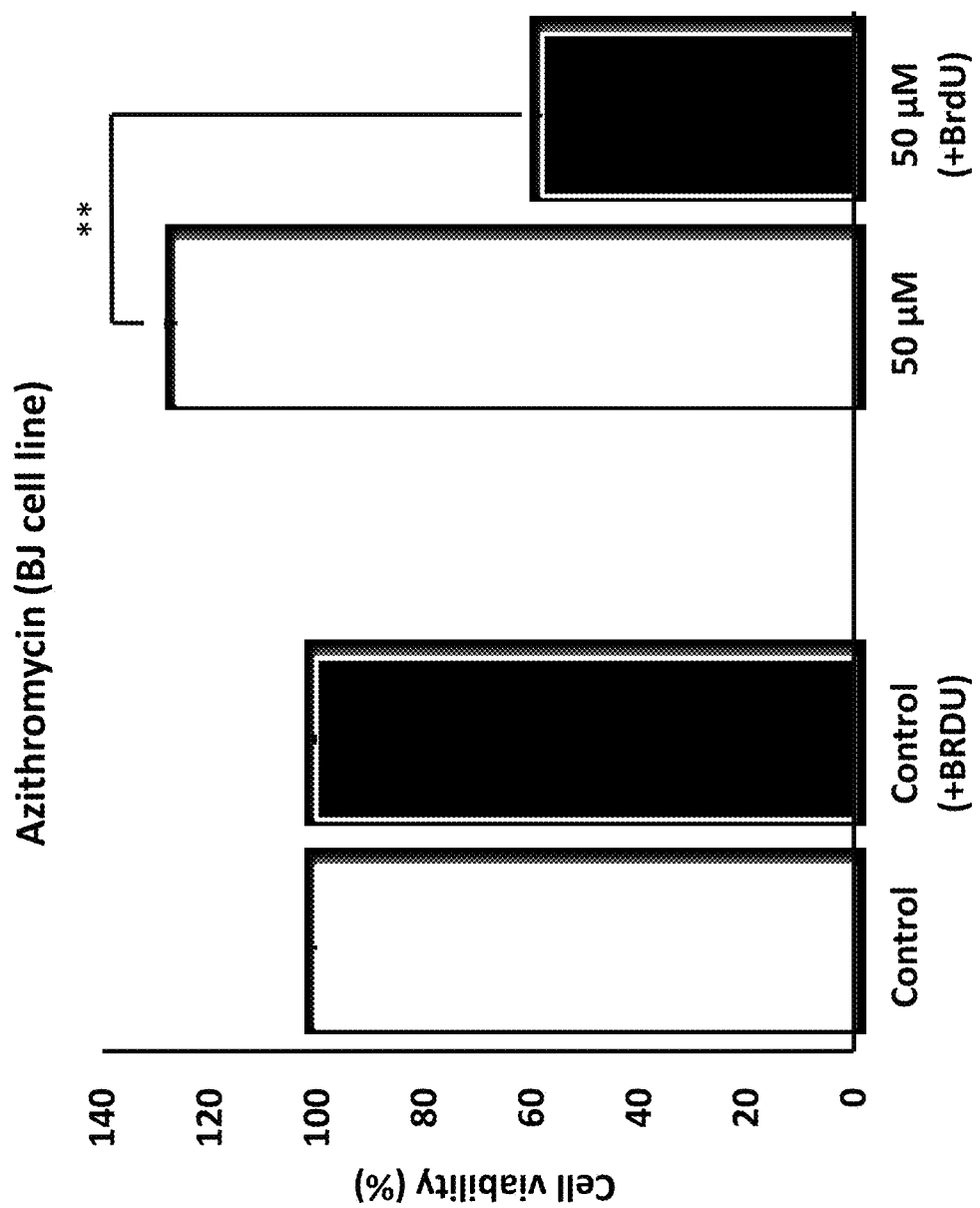
FIG. 8 shows senolytic activity in senescent human skin cells pretreated with BrdU for 8 days to induce senescence, and then exposed to azithromycin for 5 days.

The selectivity and potency of azithromycin was validated using normal, non-immortalized BJ human fibroblasts. BJ cells were pretreated with BrdU for 8 days to induce senescence, before BrdU wash out and exposure to azithromycin for 5 days. After that, the SRB assay was performed to determine the effects of azithromycin on cell viability. Azithromycin had a potent and selective effect on BJ cells, as it eliminated over 50% of senescent cells without reducing the viability of control cells after 5 days at 50 µM. These experiments were repeated at least 3 times independently, with very similar results. The results are shown in FIG. 8. Note that in FIG. 8, ** indicates p<0.01. As can be seen in FIG. 8, azithromycin was more potent in BJ skin fibroblasts, showing significant senolytic activity at only 50 µM. Azithromycin also increased the viability of normal BJ skin fibroblasts by over 25%. As such, azithromycin shows comparable selectivity and senolytic activity in human fibroblasts derived from two different anatomic sites (lung tissue and skin).

TABLE 2

Other compounds tested for senolytic activity under the present approach.

| Compounds Screened | Test Cells | Concentrations Tested |
|---|---|---|
| Doxycycline | BJ | 25-200 µM |
| Diphenyleneiodonium chloiride | BJ | 0.5-10 µM |
| Melatonin | BJ | 200-400 µM |
| Aspartame | BJ | 200-400 µM |
| Glucosamine | BJ | 10-15 µM |
| Quercetin | BJ | 10-100 µM |
| Dasatinib | BJ | 0.1-1 µM |
| Chloroquine | BJ, MRC-5 | 100-200 µM |
| Erythromycin | BJ, MRC-5 | 100-200 µM |
| Clarithromycin | BJ, MRC-5 | 100-200 µM |
| Rapamycin | MRC-5 | 50-500 µM |
| Lycopene | MRC-5 | 25-50 µM |
| Alpha-lipoic acid | MRC-5 | 25-50 µM |

The present approach was used to test a number of other drug candidates, using this senolytic assay system employing MRC-5 or BJ fibroblasts. These compounds are listed above in Table 2, which also identifies the cell line(s) used, and the range of compound concentrations used for testing. Unfortunately, none of these other drug candidates showed any specific senolytic activity, while sparing their normal fibroblast counterparts.

Although the erythromycin family as a whole does not show senolytic activity, azithromycin, roxithromycin, and telithromycin show specific and selective senolytic activity. It should be appreciated that many chemical analogs and derivatives of azithromycin, roxithromycin, and telithromycin, also possess senolytic activity. Traditionally, an 'analog' has only a single element different from a parent compound, while a 'derivative' is a chemical derived or synthesized from another. In this disclosure, the terms are used interchangeably, although many of the disclosed derivatives may also be referred to as analogs under the ordinary usage of that term. For example, a derivative in which one substitution is made to attach a targeting signal moiety may be considered an analog. It should be appreciated that derivatives having a targeting signal, such as a fatty acid membrane-targeting signal or a TPP-derivative mitochondria-targeting signal, have increased mitochondrial uptake and, as a result, increased potency. This effect is pronounced in cells heavily reliant on mitochondrial biogenesis, such as cancer stem cells and senescent cells. Compounds V through VII, below, are generic structural formula showing the location of functional groups for analogs of azithromycin, roxithromycin, and telithromycin, respectfully.

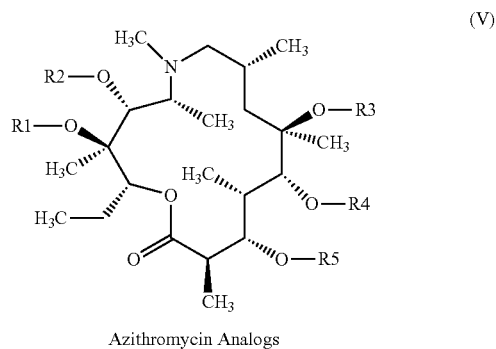

Azithromycin Analogs

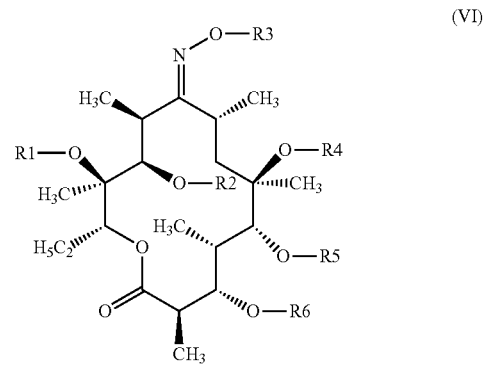

Roxithromycin Analogs

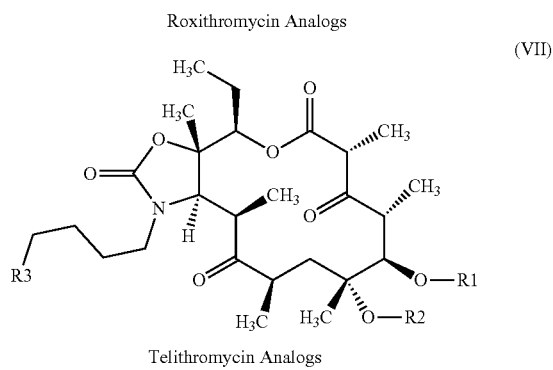

Telithromycin Analogs

Each generic structure V through VII has locations for potential conjugation or substitution, denoted by a numbered "R" and referred to as an R-group. Each R-group may be selected from hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, a membrane-targeting signal, and a mitochondria-targeting signal. It should be understood that references to a single atom, such as carbon or nitrogen, still require satisfying valence (e.g., it may require one or more additional bonds or hydrogen atoms). The term "derivative," as used herein, refers to a compound that is derived from a similar compound by a chemical reaction. One or more R-groups for a derivative senolytic compound may be substituted with a membrane-targeting signal and/or a mitochondria-targeting signal, to enhance the selectivity and effectiveness of the compound against senescent cells. Membrane-targeting signals include, for example, palmitic acid, stearic acid, myristic acid, oleic acid, short-chain fatty acids, and medium-chain fatty acids. The resulting conjugate may be synthesized according to known techniques in the art, such as lipidation reactions (e.g., myristoylation, palmitoylation, etc.), to achieve the chemical modification with a fatty acid. Mitochondria-targeting signals include, for example, lipophilic cations such as tri-phenyl-phosphonium (TPP), TPP-derivatives, guanidinium, guanidinium derivatives, and 10-N-nonyl acridine orange. Non-exhaustive examples of TPP-derivatives include 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP. Derivatives may be synthesized using techniques known in the art. It should be appreciated that these are non-exhaustive lists provided as examples.

In further application of the present approach, the selectivity of azithromycin towards senescent cells was validated using the xCELLigence system. Because senescent cells undergo the so-called senescence-associated secretory phenotype (SASP), which involves dramatic increases in the synthesis and secretion of proteins, the inventors assessed whether the protein measurement assay system under-estimates the senolytic activity of tested compounds. The xCELLigence assay system does not depend on proteins, and instead uses electrical impedance to continuously measure cell proliferation in real time.

Figure 9A:
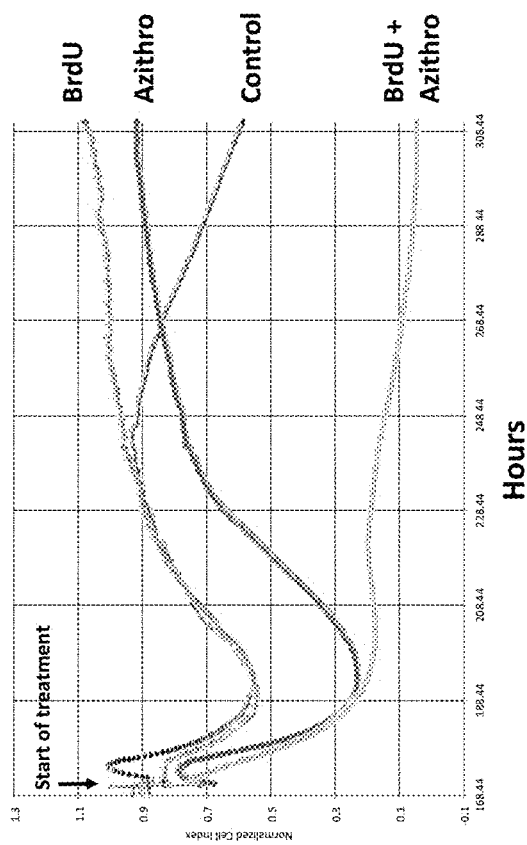
FIG. 9A shows a representative cell tracing from xCELLigence real-time cell health monitoring, for MRC-5 cell lines comparing BrdU pretreatment, BrdU pretreatment with azithromycin, azithromycin alone, and a control.
Figure 9B:
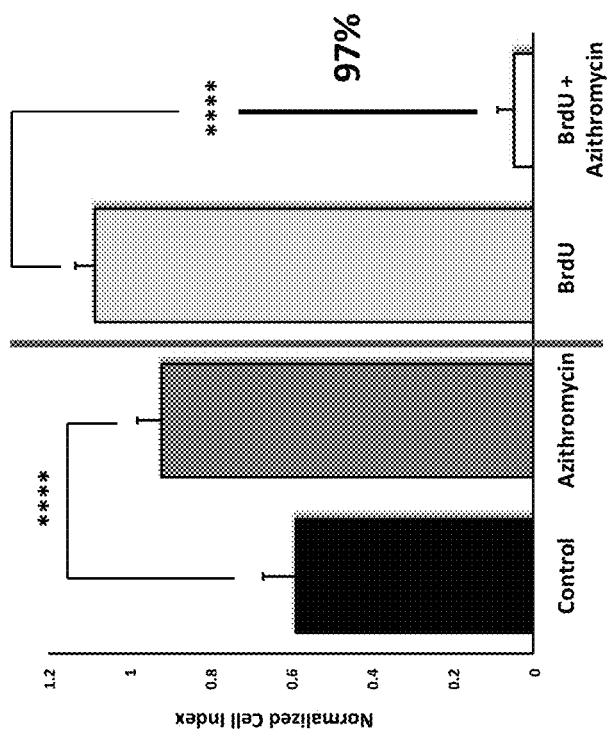
FIG. 9B summarizes final cell index results for the same lines.

FIGS. 9A and 9B show representative data from xCELLigence assays for azithromycin. The representative cell tracing in FIG. 9A shows that senescent cells (BrdU-treated/MRC-5 fibroblasts) were effectively killed. At the 308.44 hour mark, and from top-to-bottom, the curves represent cells treated with BrdU only, azithromycin only, the control, and BrdU with azithromycin. The normalized cell index for the control was noticeably higher immediately after treatment, and coincided with the BrdU-only curve until about hour 235. FIG. 9B shows bar graphs highlighting the final cell index, as the average±the standard error of mean. As can be seen, azithromycin targeted approximately 97% of the senescent MRC-5 cells. In contrast, normal control MRC-5 cells were only transiently affected by azithromycin, and they rapidly recovered via cell proliferation. The recovery shown by the cell line treated with azithromycin only exceeded the vehicle-alone control cell levels by greater than 30%. This data confirms that azithromycin preferentially targets senescent cells, removing approximately 97% of them with great efficiency—nearly a 25-fold reduction in senescent cells. For the data shown in FIGS. 9A and 9B, the **** indicates $p<0.001$. The real-time xCELLigence assay system thus compliments the more static SRB assay, and offers a more direct visualization of the potential senolytic effects of compounds during drug screening.

Figure 10A:
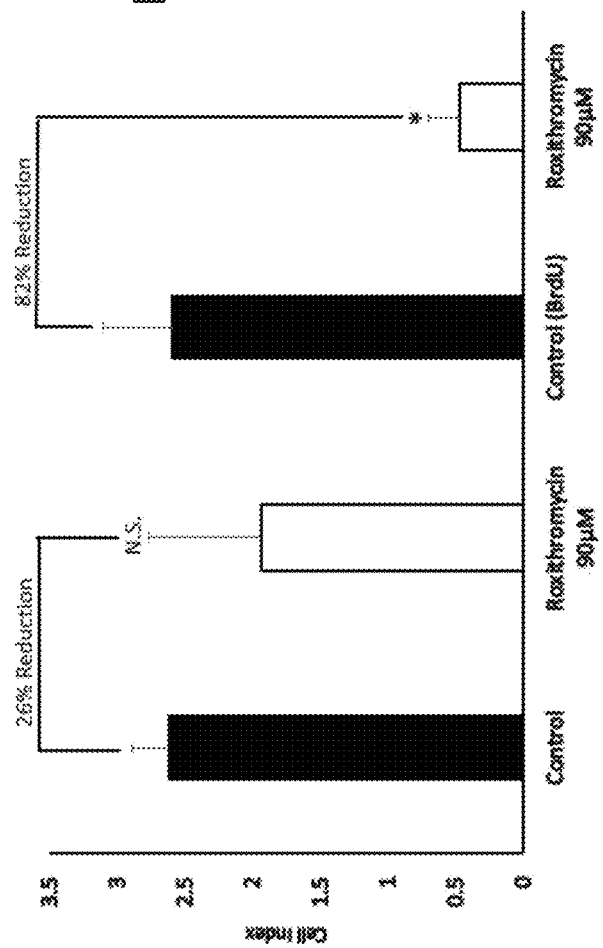
FIGS. 10A and 10B show, respectively, final cell index results and a representative cell tracing from xCELLigence real-time cell health monitoring, for MRC-5 cell lines comparing BrdU pretreatment, BrdU pretreatment with roxithromycin, roxithromycin alone, and a control.
Figure 10B:
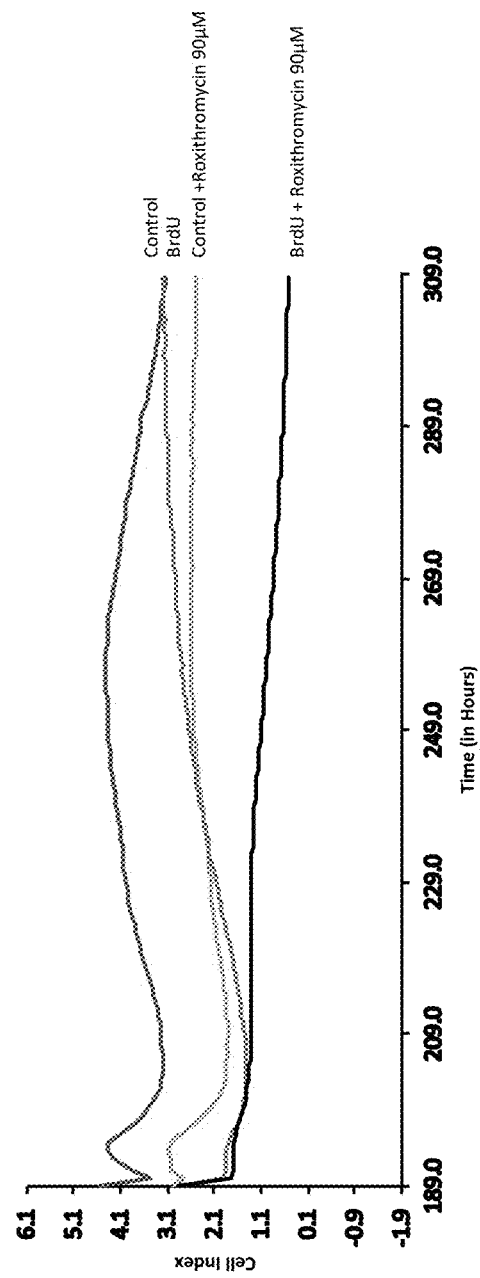

The xCELLigence assays were also used to confirm senolytic activity for roxithromycin and telithromycin. FIG. 10A shows the final cell index, as the average±the standard error of mean, for the control, roxithromycin-treated control, BrdU-treated control, and BrdU-treated fibroblasts subjected to roxithromycin at 90 μM, respectively. MRC-5 fibroblasts were used for these assays. Compared to the control, the roxithromycin treatment had minimal effect on the viability of normal fibroblasts, but targeted 82% of the fibroblasts treated with BrdU to induce senescence. The senescent MRC-5 cells were pretreated with BrdU for 8 days to induce senescence, before BrdU wash out and exposure to roxithromycin for another 5 days. These experiments were repeated at least 3 times independently, with very similar results. Note that in FIG. 10A. * indicates $p<0.01$. Representative data from xCELLigence assays for roxithromycin are shown in FIG. 10B. From top to bottom at time 249 hours, the lines represent the control, BrdU-only, Control with roxithromycin (90 μM), and BrdU with roxithromycin. As can be seen, roxithromycin caused a continuous decrease in the cell index for senescent fibroblasts. These data confirm that roxithromycin has strong senolytic activity.

Figure 11A:
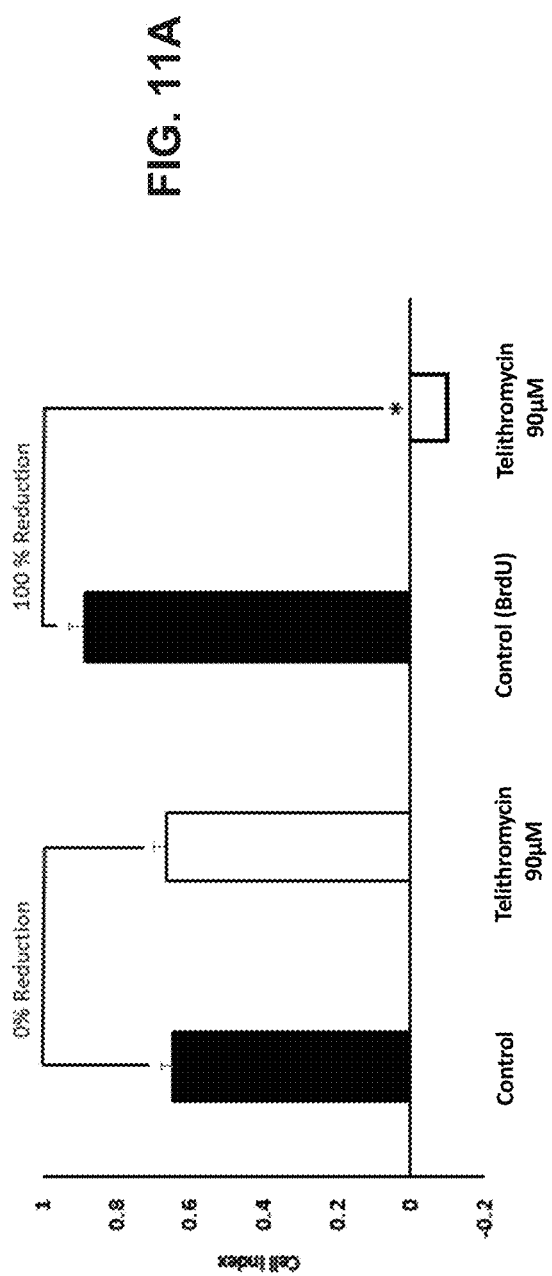
FIGS. 11A and 11B show, respectively, final cell index results and a representative cell tracing from xCELLigence real-time cell health monitoring, for MRC-5 cell lines comparing BrdU pretreatment, BrdU pretreatment with telithromycin, telithromycin alone, and a control.
Figure 11B:
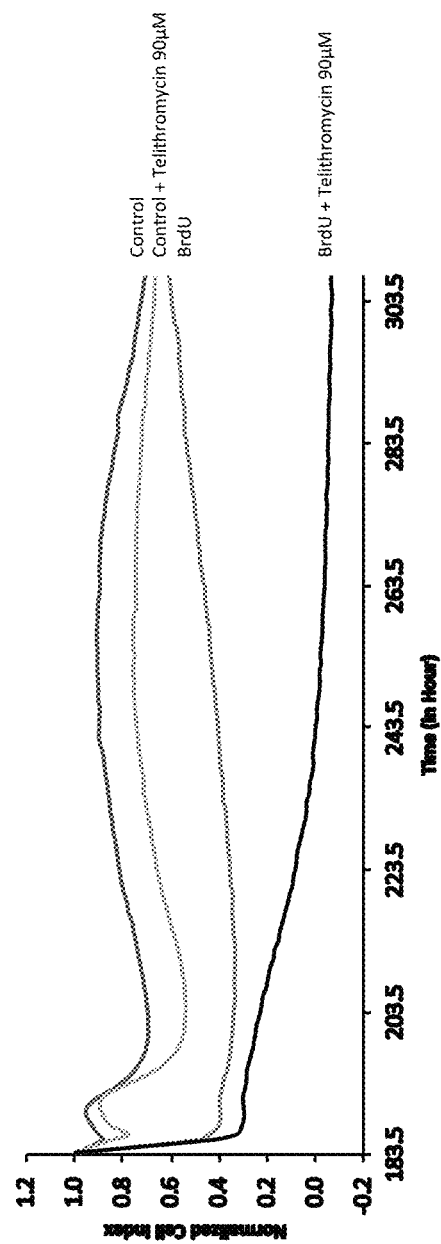

The same approach was used to confirm senolytic activity for telithromycin. FIG. 11A highlights the final cell index, as the average±the standard error of mean, and FIG. 11B shows representative xCELLigence data. Telithromycin treatments were at a concentration of 90 μM. FIG. 11A shows that telithromycin targeted 100% of the senescent cells, and had negligible impact on the normal MRC-5 cells. From top to bottom at time of 243.5 hours, FIG. 11B shows the control, control with telithromycin treatment, control with BrdU, and BrdU with telithromycin. These data demonstrate that telithromycin has strong senolytic activity.

The present approach thus provides a senolytic screening methodology to systematically identify compounds that target the senescence phenotype of human fibroblasts. As demonstrated in the data disclosed above and in the drawings, the present approach may be used to screen clinically-approved drugs, and it should be appreciated that the scope is not limited and may be used for screening other compounds. The results were generated using MRC-5 and/or BJ cells, two well-established non-immortalized human fibroblast cell lines. It should be appreciated that other human cells may be used, provided that the induction of senescence is confirmed. To induce cell cycle arrest and senescence, fibroblasts were exposed to BrdU (a DNA-damaging agent) at a concentration of 100 μM, for an 8-day period. It should be appreciated that other DNA-damaging agents may be used without departing from the present approach. The concentration and exposure duration may be varied, but it should be appreciated that senescence induction should be confirmed. After the BrdU treatment and washout, the fibroblasts were exposed to the test drug or compound. In the results discussed above, the test compound exposure was for 5 days. However, the test compound time and concentration may be varied. After drug treatment, cell attachment may be assessed via the SRB assay system, using a plate-reader, allowing high-throughput analysis. The xCELLigence assay described above may also be used.

Using the screening methodology of the present approach, the inventors demonstrated that three clinically-approved macrolide antibodies, azithromycin, roxithromycin, and telithromycin, possess senolytic activity that is highly selective towards senescent cells. In contrast, the parent compound, erythromycin, often considered to be similar in chemical structure, did not show any toxicity towards senescent fibroblasts. Metabolic analysis of the chemical effects of azithromycin showed that it induced the onset of both autophagy and glycolysis. Moreover, azithromycin increased mitochondrial activity at high dose (100 µM), but had the opposite effect at a lower dose (50 µM), demonstrating clear bi-phasic effects. These metabolic effects could underpin azithromycin's highly specific senolytic activity.

In summary, the present approach provides a screening methodology to identify compounds, such as pre-existing clinically-approved antibiotics and other drugs, having senolytic activity. The present approach may be used for drug repurposing, for example, as anti-aging drugs that can be used to target senescent fibroblasts. The present approach was used to demonstrate the selective senolytic activity of azithromycin, roxithromycin, and telithromycin. Chemical analogs of these compounds, such as may be formed using the generic chemical formula described above, also possess senolytic activity. In particular, derivatives including the addition of a membrane-targeting signal and/or a mitochondria-targeting signal, have enhanced senolytic effects.

Thus, the present approach may take the form of a method for screening compounds for senolytic activity. A cell population may be exposed to bromodeoxyuridine (BrdU) to generate or induce senescence in the cell population. The exposure may be at a BrdU concentration of 100 µM for about 8 days in some embodiments, such as described above, though the person having ordinary skill in the art can determine an appropriate exposure duration given the cell population and the BrdU concentration. The senescent cell population may be treated with a candidate compound to generate a treated cell population. The treatment duration may be about 3-5 days for some embodiments, but may vary. In some embodiments, a portion of the senescent cell population may be treated, allowing for an untreated control portion and, if desired, portions to be treated with different treatment compounds, at different compound concentrations, and/or for different treatment durations. BrdU may be washed out before treatment. It should be appreciated that the treatment compound, concentration, and treatment duration may be varied. Following treatment, the cell populations may be analyzed for indicators or markers of senolytic activity. For example, a cell population may be analyzed for cell viability, aerobic glycolysis, autophagy, inhibitory activity, quantitative measurement of autophagic LC3 proteins, and cell proliferation reduction, using assays described herein and/or known in the art. Either or both the Sulphorhodamine B assay and measuring cell-induced electrical impedance may be used to analyze senolytic activity, as further examples. It should be appreciated that the person having ordinary skill in the art may deviate from the assays described herein to assess the senolytic activity of a treatment compound.

The present approach may also take the form of a senolytic composition having a therapeutic amount of at least one senolytic agent. The senolytic agent may be azithromycin, roxithromycin, telithromycin, an azithromycin analog, a roxithromycin analog, and a telithromycin analog. It is to be understood that a therapeutic amount may be determined by the person having ordinary skill in the art, using this disclosure and methods known and available in the art. In some embodiments, the senolytic agent may be substituted with at least one targeting signal, which may be either (i) a membrane-targeting signal selected from palmitic acid, stearic acid, myristic acid, oleic acid, a short-chain fatty acid, and a medium-chain fatty acid; or (ii) a mitochondria targeting signal selected from tri-phenyl-phosphonium (TPP), a TPP-derivative, guanidinium, guanidinium derivatives, and 10-N-nonyl acridine orange. The targeting signal substitution enhances the senolytic activity through increasing the mitochondrial uptake of the senolytic agent. For example, an R-group shown in any of compounds IV-VI, above, may comprise a targeting signal. In some embodiments, the targeting signal may be a TPP-derivative attached to the senolytic compound at one of the substitution locations. Examples of TPP-derivatives include, but are not limited to, 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP. It should be appreciated that substitution with a TPP-derivative may require covalent bonding.

In some embodiments, the senolytic agent may include a tetracycline compound, including tetracycline, chlortetracycline, oxytetracycline, demeclocycline, methacycline, doxycycline, minocycline, and tigecycline. These mitochondrial biogenesis inhibitors may be used to inhibit oxidative metabolism, and further amplify the senolytic activity. Data and further examples are described in International Application No. PCT/US2018/028587, filed Apr. 20, 2018, which is incorporated by reference in its entirety. In some embodiments, the senolytic agent may include a glycolysis inhibitor, such as, for example, pyrvinium, atovaquone, bedaquiline, irinotecan, sorafenib, niclosamide, stirpentol, chloroquine, and rapamycin. As discussed above, senescent cells treated with a senolytic agent transition to a glycolytic phenotype. The introduction of a glycolysis inhibitor deprives these cells of a functional metabolic pathway, and thereby enhance the induction of cell death in the senescent cell population.

Under the present approach, a number of mitochondrial biogenesis inhibitors may be used in connection with a senolytic agent. Further examples of mitochondrial inhibitors include: mitoriboscins, oxidative metabolism inhibitors and glycolytic metabolism inhibitors, repurposcins, antimitoscins, mitoketoscins, mitoflavoscins, mitoflavins, TPP-derivatives, MDIVI-1 derivatives, chloramphenicol, puromycin and other inhibitors of protein synthesis (including, e.g., aminoglycosides and rapamycin analogs), anti-parasitic drugs (such as, e.g., pyrvinium pamoate, and niclosamide), chloroquine, stiripentol, caffeic acid phenyl ester (CAPE), Vitamin C, 2-Deoxy-Glucose (2-DG), MCT1 inhibitors (AZD3965 and AR-C155858), D-Glucosamine, quercetin, and carvedilol. The following paragraphs describe certain categories of mitochondrial biogenesis inhibitor therapeutics. For brevity, related co-pending applications are incorporated by reference as if fully set forth herein.

A first category of mitochondrial biogenesis inhibitors are mitoriboscins, as described in International Application No. PCT/US2018/022403, filed Mar. 14, 2018, and incorporated by reference in its entirety. The incorporated reference includes data for select mitoriboscin compounds. Generally, mitoriboscins are mitochondrial inhibitor compounds that have anti-cancer and often antimicrobial activity, chemotherapy-sensitizing, radiosensitizing, and photosensitizing effects, as well as anti-aging effects. These compounds bind to either the large sub-unit or the small sub-unit of the mitochondrial ribosome (or in some instances, both) and inhibit mitochondrial biogenesis. Examples of mitoriboscin groups, along with generic chemical structures and specific compounds, are described in the incorporated application, and include mitoribocyclines, mitoribomycins, mitoribosporins, and mitoribofloxins. Demonstrative mitoriboscins are shown below as compounds VIII-XVII.

(VIII)

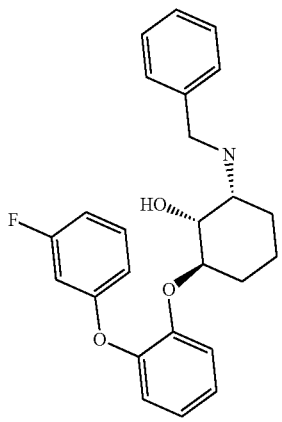

Mitroriboscin Compound 23/E9

(IX)

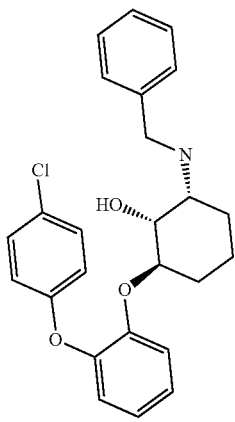

Mitoriboscin Compound 23/G4

(X)

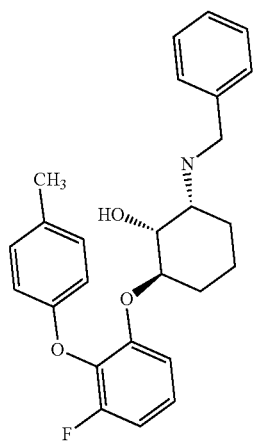

Mitoriboscin Compound 24/B10

(XI)

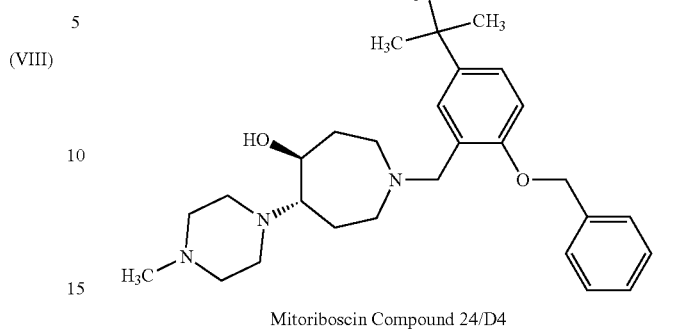

Mitoriboscin Compound 24/D4

(XII)

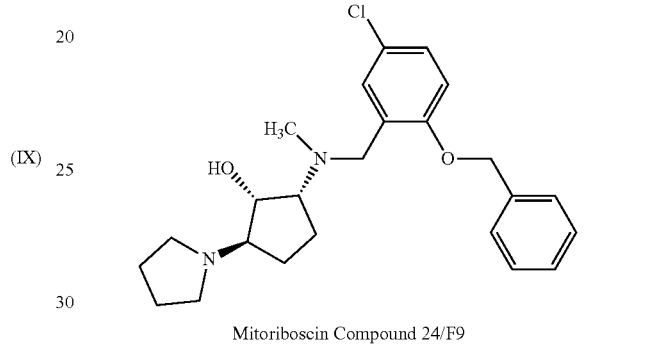

Mitoriboscin Compound 24/F9

(XIII)

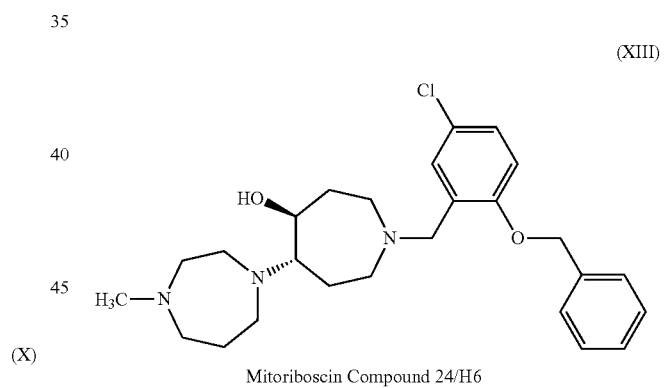

Mitoriboscin Compound 24/H6

(XIV)

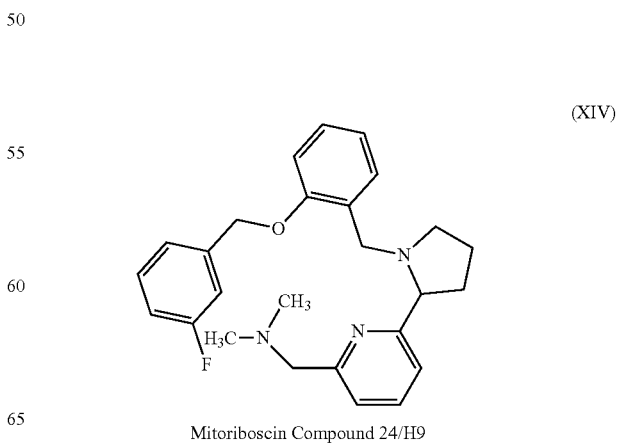

Mitoriboscin Compound 24/H9

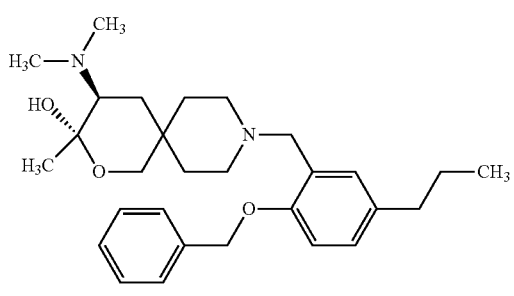

Compound 25/B3

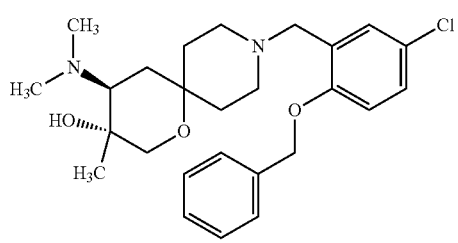

Mitoriboscin Compound 25/E3

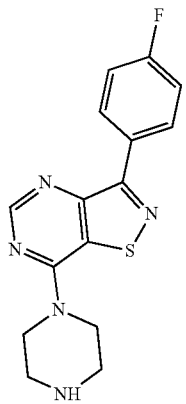

Mitoriboscin Compound 26/H4

Mitoketoscins are another category of mitochondrial biogenesis inhibitors that may be used to enhance senolytic activity. These are non-carcinogenic compounds that bind to at least one of ACAT1/2 and OXCT1/2 and inhibit mitochondrial ATP production. These compounds are described more fully in International Application PCT/US2018/039354, filed Jun. 25, 2018, and incorporated by reference in its entirety. Generally, a mitoketoscin targets the mitochondrial enzymes responsible for ketone re-utilization and that have anti-cancer and antibiotic properties. These compounds bind to either or both active catalytic sites of OXCT1/2 and ACAT1/2 to inhibit mitochondrial function.

Repurposcins and antimitoscins are a third category of mitochondrial biogenesis inhibitors that may be used in connection with the present approach. International Patent Application PCT/US2018/062956, filed Nov. 29, 2018 and incorporated by reference in its entirety, describes repurposcins more fully. Generally, "repurposcins" are compounds having intrinsic anti-mitochondrial properties that are chemically modified to target the compounds to mitochondria. Antimitoscins, a category of repurposcins, are described more fully in International Patent Application PCT/US2018/033466, filed May 18, 2018 and incorporated by reference in its entirety. Existing antibiotics having intrinsic anti-mitochondrial properties can be chemically modified to target the mitochondria and inhibit mitochondrial biogenesis. The term "antimitoscin" broadly refers to an antibiotic having intrinsic anti-mitochondrial properties that is chemically modified to target the antibiotic to mitochondria. Previously, intrinsic anti-mitochondrial activity in antibiotics was considered to be an unwanted side-effect. Indeed, some potential antibiotics have been excluded from trials due to excessive anti-mitochondrial properties, and researchers have viewed anti-mitochondrial activity as a potential drawback. However, under the present approach, an antibiotic's intrinsic anti-mitochondrial activity can become the basis for an entirely new therapeutic. The antimitoscin may be an antibiotic having intrinsic anti-mitochondrial properties chemically modified with a mitochondrial targeting signal (e.g., a chemical moiety). Chemical modification may be, for example, through covalent or non-covalent bonds. In some embodiments, the antibiotic is one of a member of the tetracycline family, the erthyromycin family, chloramphenicol, pyrvinium pamoate, atovaquone, and bedaquiline. The mitochondria-targeting signal may be at least one compound or moiety selected from the group comprising a membrane targeting signal and a mitochondrial ribosome-targeting signal. Examples of membrane targeting signals include short-chain (e.g., fewer than 6 carbon atoms in the chain) fatty acids and medium-chain (e.g., 6-12 carbon atoms in the chain) fatty acids, palmitic acid, stearic acid, myristic acid, and oleic acid. Examples of mitochondrial ribosome-targeting signals include tri-phenyl-phosphonium (TPP) and guanidinium-based moieties. TPP and guanidinium are non-toxic chemical moieties that functionally behave as a mitochondrial targeting signal (MTS) in living cells. Either may be bonded to an antibiotic, often through the use of a carbon spacer-arm or linking chain.

Mitoflavoscins and mitoflavins are a fourth category of mitochondrial biogenesis inhibitors that may be used under the present approach. These compounds are described more fully in International Patent Application PCT/US2018/057093, filed Oct. 23, 2018 and incorporated by reference in its entirety. Mitoflavoscins are compounds that bind to flavin-containing enzymes and inhibit mitochondrial ATP production. Diphenyleneiodonium chloride (DPI) is an example of a mitoflavoscin. It should be appreciated that a mitoflavoscin may be modified with a mitochondrial targeting signal, such as discussed above with respect to antimitoscins. Mitoflavins, derivatives of riboflavin that inhibit mitochondrial function, may also be chemically modified with a mitochondrial targeting signal. For example, roseoflavin [8-Demethyl-8-(dimethylamino)-riboflavin or 8-Dimethylaminoriboflavin] is a naturally occurring anti-bacterial compound that is a derivative of riboflavin, which can be chemically modified to optimize its potential for targeting CSCs and inhibiting mitochondrial biogenesis. Lumichrome (7,8-Dimethylalloxazine) is a fluorescent photoproduct of riboflavin degradation, which also can be chemically modified to optimize its potential for targeting CSCs. Other common derivatives of riboflavin include: Alloxazine, Lumiflavine, 1,5-dihydroriboflavin and 1,5-dihydroflavin. Each of these riboflavin derivatives may be chemically modified with a mitochondrial targeting signal to form a mitoflavin, and may be used as a mitochondrial biogenesis inhibitor according to the present approach.

A sixth category of mitochondrial biogenesis inhibitors is TPP-derivative compounds that show not only a strong preference for uptake in cancer cells (bulk cancer cells, cancer stem cells, and energetic cancer stem cells), but also disrupt mitochondrial biogenesis in these cells. These TPP-derivative compounds are described more fully in International Patent Application PCT/US2018/062174, filed Nov. 21, 2018 and incorporated by reference in its entirety. As used with respect to TPP-derivatives, a derivative as known in the art is a compound that can be synthesized from a parent compound by replacing an atom with another atom or group of atoms. For example, a derivative of TPP is 2-butene-1,4-bis-TPP, which includes two phosphonium groups joined by butene. A derivative of 2-butene-1,4-bis-TPP, then, could include replacement of one or more phenyl groups with another compound, such as a halogen or an organic compound. For the sake of brevity, this disclosure does not identify all of the potential derivatives, as the description should be adequate for a person of ordinary skill in the art. Other examples of TPP-derivative compounds that may be used as mitochondrial biogenesis inhibitors according to the present approach include 2-butene-1,4-bis-TPP; derivatives of 2-butene-1,4-bis-TPP; 2-chlorobenzyl-TPP; derivatives of 2-chlorobenzyl-TPP; 3-methylbenzyl-TPP; derivatives of 3-methylbenzyl-TPP; 2,4-dichlorobenzyl-TPP; derivatives of 2,4-dichlorobenzyl-TPP; 1-naphthylmethyl-TPP; derivatives of 1-naphthylmethyl-TPP; p-xylylenebis-TPP; and derivatives of p-xylylenebis-TPP. Of course, it should be appreciated that the foregoing list is not an exhaustive list of TPP-derivatives.

Another category of mitochondrial biogenesis inhibitors that may be used in the present approach is MDIVI-1 derivatives, as described in International Patent Application PCT/US2018/066247, filed Dec. 18, 2018 and incorporated by reference in its entirety. Mitochondrial division inhibitor-1 (mDIVI-1) is a small molecule that selectively and reversibly inhibits DRP1. MDIVI-1 has been shown to target DRP1 by binding and suppressing both the DRP1 self-assembly into ring-like structures around the mitochondria and its capacity to catalyze GTP hydrolysis. The present approach may take the form of a mitochondrial fission inhibitor 1 (mDIVI-1) derivative having the general formula XVIII shown below:

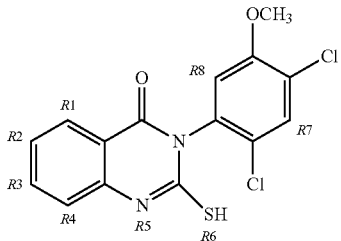

(XVIII)

or a pharmaceutically acceptable salt thereof, wherein each of R1 through R8 may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, and a mitochondrial targeting signal. In some embodiments, at least one R-group is a targeting signal, such as those described above.

Examples of other mitochondrial biogenesis inhibitors that may be used under the present approach to enhance the activity of a senolytic agent include Vitamin C, berberine, caffeic acid phenyl ester, silibinin, brutieridin, and melitidin.

It should be appreciated that senolytic compositions have a wide range of advantageous uses. For example, a senolytic composition may be used in senescence therapy, which constitutes the treatment of senescent cells through, e.g., inducing death of senescent cells, and/or inhibiting the propagation of senescent cells. A senolytic composition may be used to delay the onset and/or progression of an age-related disease, such as atherosclerosis, arthritis, cancer, cardiovascular disease, cataract, dementia, diabetes, hair loss, hypertension, inflammatory disease, kidney disease, muscular atrophy, osteoarthritis, osteoporosis, pulmonary disease, vertebral disc degeneration, and alopecia. Neurological diseases such as mild cognitive impairment, motor neuron dysfunction, Alzheimer's disease, Parkinson's disease, and macular degeneration, may also be treated or delayed through the use of a senolytic composition. In some instances, a senolytic composition may be used to treat an age-related disease.

A senolytic agent may take numerous forms. For example, a senolytic agent may take the form of a cosmetic, a pill, a lotion, a shampoo, a cream, a soap, a skin cleaner, a shaving preparation, an after-shave, a gel, a stick, a paste, a spray, an aerosol, a powder, a liquid, an aqueous suspension, an aqueous solution, a foam, a transdermal patch, a tincture, and a vapor. For example, a senolytic composition for treating hair loss may take the form of a topical application for hair, the scalp, and/or skin. It should be appreciated that the person having ordinary skill in the art is familiar with selecting the form of the senolytic agent, using methods known and available in the art that need not be repeated herein.

As discussed above, derivatives of azithromycin, roxithromycin, and telithromycin, may be used as senolytics without departing from the present approach. In some embodiments, the derivative may involve one or more substituted targeting signals. The addition of a membrane-targeting signal or a mitochondria-targeting signal to azithromycin, roxithromycin, or telithromycin, significantly increases mitochondrial uptake of the resulting conjugate, and consequently improves the senolytic activity. For example, compounds XIX-XXI, shown below, demonstrate derivatives in which one or more functional R-groups is a targeting signal.

First, compound XIX shows a general formula for azithromycin derivatives according to some embodiments, in which either functional group R1 or R2 may be the same or may be different, and one or both is a targeting signal. For example, R1 and/or R2 may be a membrane-targeting signal selected from palmitic acid, stearic acid, myristic acid, oleic acid, a short-chain fatty acid, and a medium-chain fatty acid. (Of course, the conjugate would include a moiety in which the terminal hydrogen is removed for bonding, such as a palmitate salt). R1 and/or R2 may be a mitochondria-targeting signal, selected from tri-phenyl-phosphonium (TPP), TPP-derivatives, guanidinium, guanidinium derivatives, and 10-N-nonyl acridine orange. Non-exhaustive examples of TPP-derivatives include 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP. In some embodiments, only one of R1 and R2 deviates from the parent compound, and thus the derivative is an analog. For example, R1 may be methyl and R2 may be a targeting signal. As another example, R1 may be a targeting signal and NH—R2 may be —N(CH$_3$)$_2$. In some embodiments, either R1 or R2 may be a targeting signal, and the other of R1 and R2 may be selected from consisting of hydrogen, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives.

derivatives, monocyclic or polycyclic arenes, heteroarenes, arene-based derivatives, heteroarene-based derivatives, phenols, phenol-based derivatives, benzoic acid, and benzoic acid-based derivatives.

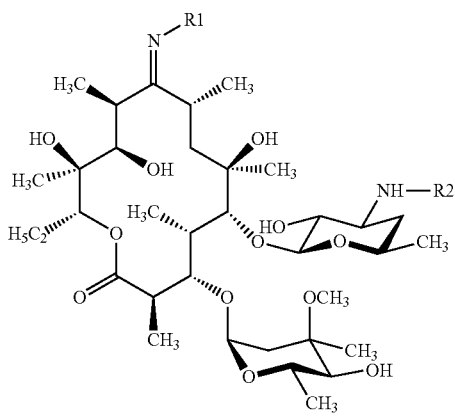

(XX)

Roxithromycin derivative

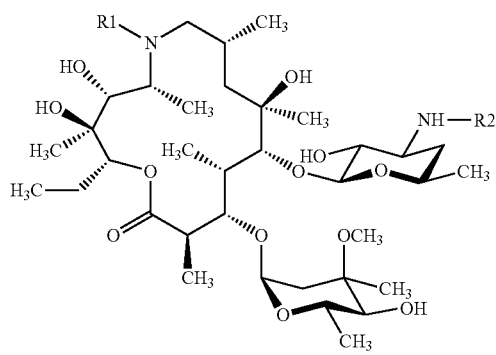

(XIX)

Azithromycin derivative

Compound XX shows a general formula for roxithromycin derivatives according to some embodiments, in which either functional group R1 or R2 may be the same or may be different, and one or both may be a targeting signal. For example, R1 and/or R2 may be a membrane-targeting signal or a mitochondria-targeting signal, as discussed above. In some embodiments, only one of R1 and R2 deviates from the parent compound, and thus the derivative is an analog. For example, R1 may be a methoxy, such as O—CH$_2$—O—(CH$_2$)$_2$—OCH$_3$ present in roxithromycin, and R2 may be a targeting signal. As another example, R1 maybe a targeting signal and NH—R2 may be N(CH$_3$)$_2$. In some embodiments, either R1 or R2 may be a targeting signal, and the other of R1 and R2 may be selected from consisting of hydrogen, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based Compound XXI shows a general formula for telithromycin derivatives, in which either functional group R1 or R2 may be the same or may be different, and one or both may be a targeting signal. For example, R1 and/or R2 may be a membrane-targeting signal or a mitochondria-targeting signal, as discussed above. In some embodiments, only one of R1 and R2 deviates from the parent compound, and thus the derivative is an analog. For example, R1 may be an alkyl-aryl group, such as

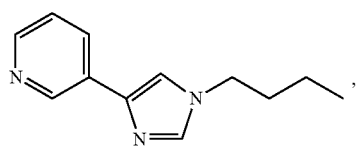

which is present on the telithromycin carbamate ring, and R2 may be a targeting signal. As another example, R1 maybe a targeting signal and —NH—R2 may be —N(CH$_3$)$_2$. In some embodiments, either R1 or R2 may be a targeting signal, and the other of R1 and R2 may be selected from consisting of hydrogen, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives.

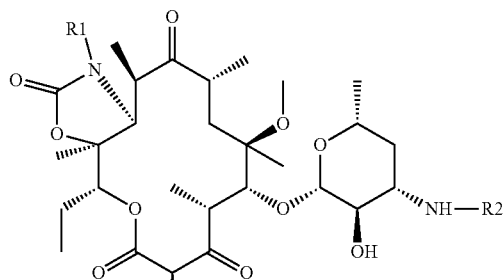

Telithromycin derivative (XXI)

The example below, compound XXII, shows an azithromycin derivative, in which R1 is methyl, and R2 is a fatty acid membrane targeting signal. In this example, R2 is a fatty acid moiety, from membrane-targeting signal myristic acid. It should be appreciated that compound XXII may be formed, as an example, through myrostoylation, a lipidation technique known in the art. This example of a senolytic compound has increased mitochondrial uptake relative to azithromycin, and as a result increased senolytic activity. Compound XXII is one example of an azithromycin derivative under the present approach having senolytic activity. It should be appreciated that numerous other derivatives having senolytic activity may be made under the present approach.

thromycin (from GSK and Sandoz) is not available in the United States, but is clinically-approved in New Zealand, Australia and Israel.

MRC-5 or BJ cells were plated into 24-well plates. Next day, half of the plate was treated with 100 μM of BrdU while control wells were treated with vehicle only (DMSO) and incubated for 8 days at 37° C. in a 5% $CO_2$ humidified atmosphere. After 8 days of BrdU treatment cells were treated with various test compounds or drugs (e.g., azithromycin, roxithromycin, telithromycin, erythromycin, etc.) for another 3-5 days. BrdU is washed out before the drug treatments.

Sulphorhodamine B assay: After the incubation of the plates cell viability was measured by Sulphorhodamine B assay (SRB). The assay is based on the measurement of cellular protein contents. Cells were fixed with 10% Trichloroacetic acid (TCA) for 1 hour at 4oC, and were dried overnight at room temperature. Then, plates were incubated with SRB for 30 min, washed twice with 1% acetic acid and air dried for at least 1 h. Finally, the protein-bound dye was dissolved in a 10 mM Tris, pH 8.8, solution and read using a plate reader at 540-nm.

Autophagy and Cell cycle analysis: Autophagy (using Muse™M Autophagy LC3-antibody based Kit, Merck Millipore) and cell cycle (Muse® Cell Cycle Kit, Merck Millipore) experiments were performed according to manufacturer's instructions.

Beta-Gal staining: Beta-Galactosidase staining of BrdU-treated MRC-5 cells was performed by Senescence B-Galactosidase Staining Kit (#9860, Cell Signalling Technology Inc.) and was done according to manufacturer's protocol.

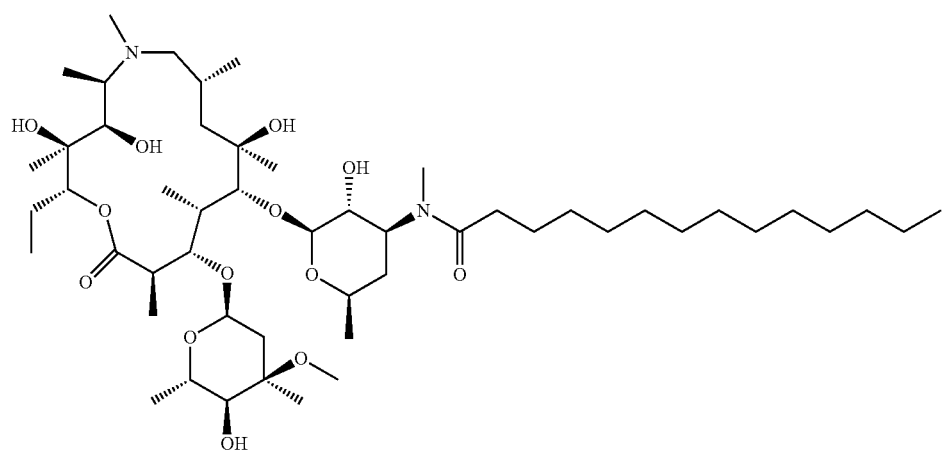

(XXII)

The following paragraphs describe the materials and methods used in connection to the experiments and data disclosed herein. It should be appreciated that these materials and methods are demonstrative, and that the person having an ordinary level of skill in the art may deviate without departing from the present approach. MRC-5 (ATCC® CCL-171) human lung fibroblast cells and BJ (ATCC® CRL2522) human skin fibroblasts were purchased from the ATCC (American Type Culture Collection). Gibco-brand cell culture media (MEM) was purchased from Life Technologies. Bromodeoxyuridine, azithromycin, roxithromycin and erythromycin were purchased from Sigma-Aldrich. Azithromycin (from Pfizer) is FDA-approved. Roxi- Seahorse XFe96 metabolic flux analysis: Extracellular acidification rates (ECAR) and real-time oxygen consumption rates (OCR) for MCF7 cells were determined using the Seahorse Extracellular Flux (XF96) analyzer (Seahorse Bioscience, MA, USA). MRC-5 cells were maintained in MEM supplemented with 10% FBS (foetal bovine serum), 2 mM GlutaMAX, and 1% Pen-Strep. 40,000 cells per well were seeded into XF96-well cell culture plates, and incubated overnight at 37° C. in a 5% CO2 humidified atmosphere. Next day, cells were treated with Azithromycin for 72 hours. Before the experiment, plate was washed with pre-warmed XF assay media (for OCR measurement, XF assay media was supplemented with 10 mM glucose, 1 mM Pyruvate and adjusted at pH 7.4). Cells were then maintained in 175

µL/well of XF assay media at 37° C., in a non-CO2 incubator for 1 h. During incubation, 25 µL of 80 mM glucose, 9 µM Oligomycin, 1M 2-deoxyglucose (for ECAR measurement) and 25 µL of 10 µM Oligomycin, 9 µM FCCP. 10 µM Rotenone, 10 µM Antimycin A (for OCR measurement) in XF assay media was loaded into the injection ports of the XFe-96 sensor cartridge. During the experiment, the instrument injected these inhibitors into the wells at a given time point, while ECAR/OCR was measured continuously. ECAR and OCR measurements were normalized by protein content (Sulphorhodamine B assay). Data sets were analyzed by XFe-96 software, using one-way ANOVA and Student's t-test calculations. All experiments were performed at least in triplicate for the results disclosed herein.

The xCELLigence Assay System: xCELLigence RTCA System (ACEA Biosciences Inc.). Briefly, MRC-5 lung fibroblasts (vehicle alone and/or treated with 100 µM BrdU) were seeded in each well and employed to assess the efficacy of Azithromycin, using RTCA (real-time cell analysis), via the measurement of cell-induced electrical impedance. This approach allows the quantification of the onset and kinetics of the cellular response. Experiments were repeated several times independently, using quadruplicate samples for each condition.

Statistical analyses: Statistical significance was determined using the Student's t-test; values of less than 0.05 were considered significant. Data are shown as the mean±SEM.

The terminology used herein is for the purpose of describing particular embodiments only and is not intended to be limiting of the approach. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

What is claimed is:

1. A method for inducing death of senescent cells in a subject, the method comprising administering to the subject a therapeutic amount of a compound having a formula selected from the group consisting of:

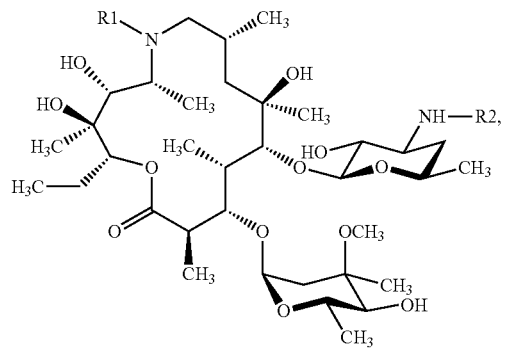

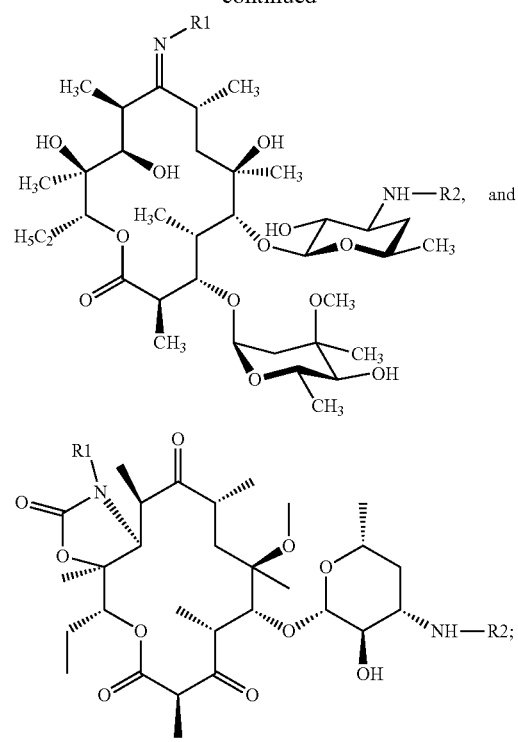

wherein R1 and R2 may be the same or different, and are selected from a membrane-targeting signal, a mitochondria-targeting signal, hydrogen, carboxyl, an alkane, a cyclic alkane, an alkene, a cyclic alkene, an alkyne, a ketone, an aldehyde, a carboxylic acid, an ether, an ester, an amine, an amide, a monocyclic arene, a polycyclic arene, a heteroarene, and a benzoic acid; and at least one of R1 and R2 is selected from the group consisting of palmitic acid, stearic acid, myristic acid, and oleic acid.

2. The method of claim 1, wherein at least one of R1 and R2 is myristic acid.

3. The method of claim 1, wherein the compound has a formula:

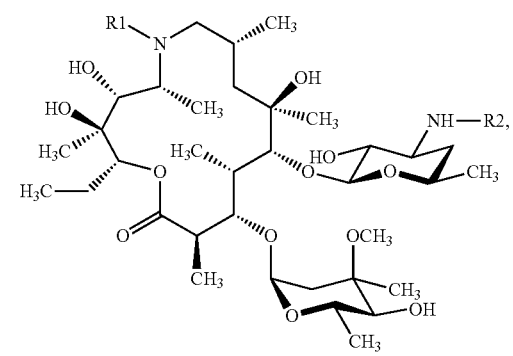

wherein R1 is methyl and R2 is selected from the group consisting of palmitic acid, stearic acid, myristic acid, and oleic acid.

4. The method of claim 1, wherein the compound has a formula:

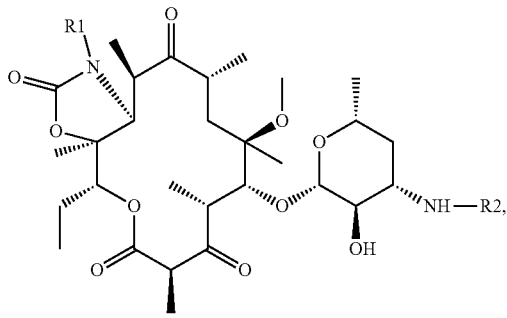

wherein R1 is

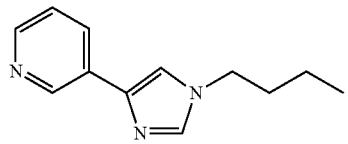

and R2 is selected from the group consisting of palmitic acid, stearic acid, myristic acid, and oleic acid.

5. The method of claim 1, further comprising administering a therapeutic amount of at least one of tetracycline, chlortetracycline, oxytetracycline, demeclocycline, methacycline, doxycycline, minocycline, and tigecycline.

6. The method of claim 1, further comprising administering a therapeutic amount of at least one of pyrvinium, atovaquone, bedaquiline, irinotecan, sorafenib, niclosamide, stirpentol, chloroquine, and rapamycin.

7. The method of claim 1, further comprising administering a therapeutic amount of at least one of a mitoriboscin, a mitoketoscin, a mitoflavoscin, 2-butene-1,4-bis-TPP; a derivative of 2-butene-1,4-bis-TPP; 2-chlorobenzyl-TPP; 3-methylbenzyl-TPP; 2,4-dichlorobenzyl-TPP; and 1-naphthylmethyl-TPP.

8. The method of claim 1, further comprising administering at least one of Vitamin C, berberine, caffeic acid phenyl ester, silibinin, brutieridin, and melitidin.

* * * * *